US005744132A

United States Patent [19]

Warne et al.

[11] Patent Number: 5,744,132
[45] Date of Patent: Apr. 28, 1998

[54] FORMULATIONS FOR IL-12

[75] Inventors: Nicholas W. Warne, Methuen; Thomas J. Crowley, Malden; Tracy M. Smith, Lawrence, all of Mass.

[73] Assignee: Genetics Institute, Inc., Cambridge, Mass.

[21] Appl. No.: 783,523

[22] Filed: Jan. 14, 1997

Related U.S. Application Data

[63] Continuation of Ser. No. 384,062, Feb. 6, 1995, abandoned.
[51] Int. Cl.⁶ ................................................ A61K 45/05
[52] U.S. Cl. ................................................ 424/85.2
[58] Field of Search ........................................ 424/85.2

[56] References Cited

U.S. PATENT DOCUMENTS

| | | | |
|---|---|---|---|
| 4,496,537 | 1/1985 | Kwan | 424/85 |
| 4,675,183 | 6/1987 | Lato | 424/85 |
| 5,104,651 | 4/1992 | Boone et al. | 424/85.1 |
| 5,215,743 | 6/1993 | Singh et al. | 424/85.1 |
| 5,358,708 | 10/1994 | Patel | 424/85.1 |
| 5,457,038 | 10/1995 | Trinchieri et al. | 435/69.52 |

FOREIGN PATENT DOCUMENTS

| | | |
|---|---|---|
| 3723781 | 1/1988 | Germany . |
| 4242919 | 6/1994 | Germany . |
| 6-247870 | 9/1994 | Japan . |
| 9323065 | 11/1993 | WIPO . |

OTHER PUBLICATIONS

Stern et al., PNAS, vol. 87, pp. 6808–6812, 1990.
Wang et al., J. Parenteral Sci & Tech, vol. 42(25), pp. s3–s26, 1988.
Manning et al., Pharm. Res., vol. 6(11), pp. 903–918, 1989.
Pikal, Bio Pharm, vol. 3(9), pp. 26–30, Oct. 1990.

*Primary Examiner*—Chhaya D. Syala
*Attorney, Agent, or Firm*—Scott A. Brown; Thomas J. DesRosier

[57] ABSTRACT

Provided by the present invention are novel compositions and methods for obtaining concentrated preparations of IL-12 and formulations of IL-12 suitable for storage and administration.

4 Claims, 17 Drawing Sheets

1. mwm
2. 2853-94 rhIL-12 ref. std.
3. pH 3.5 @ 30°C
4. pH 4.5 @ 30°C
5. pH 5.5 @ 30°C
6. pH 6.5 @ 30°C
7. pH 7.2 @ 30°C
8. pH 8.3 @ 30°C
9. pH 9.6 @ 30°C

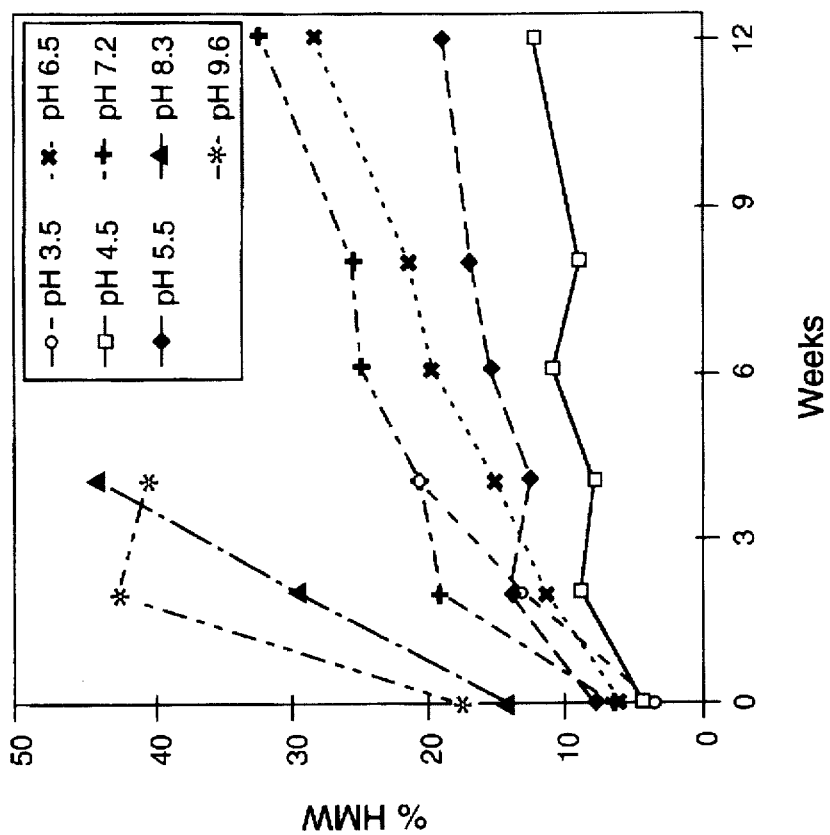
Fig. 2-B
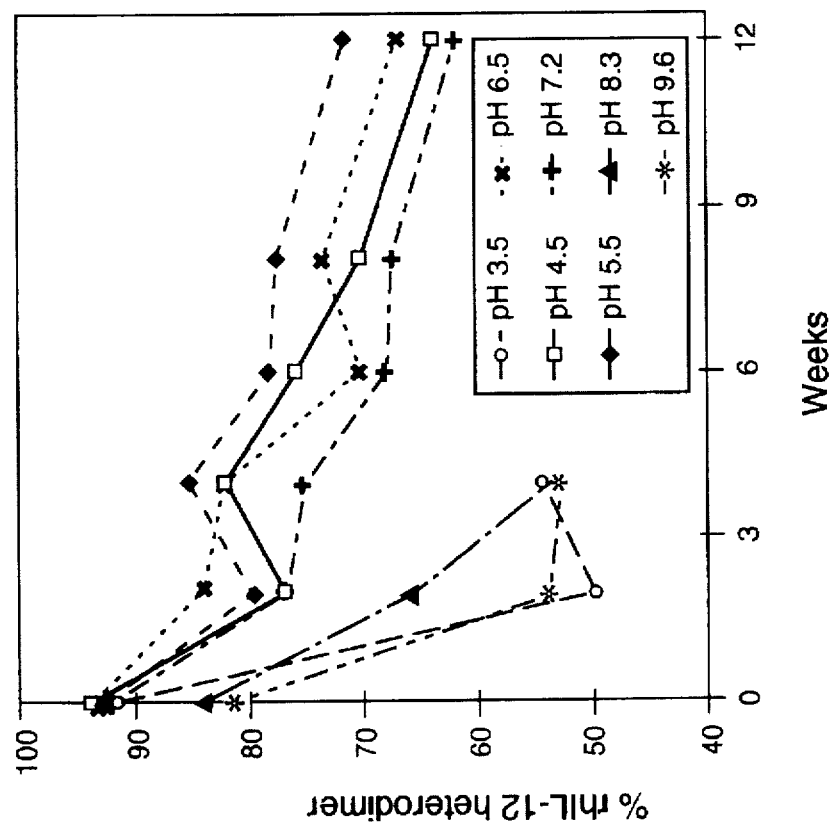
Fig. 2-A

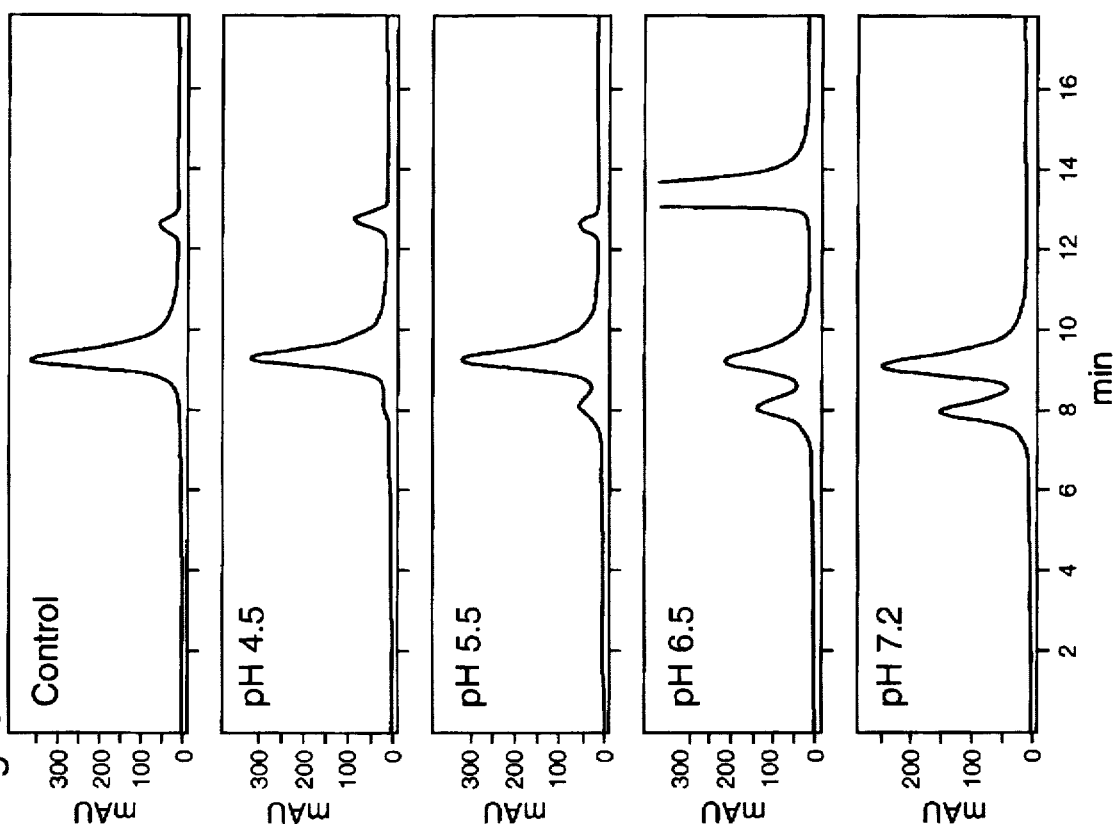
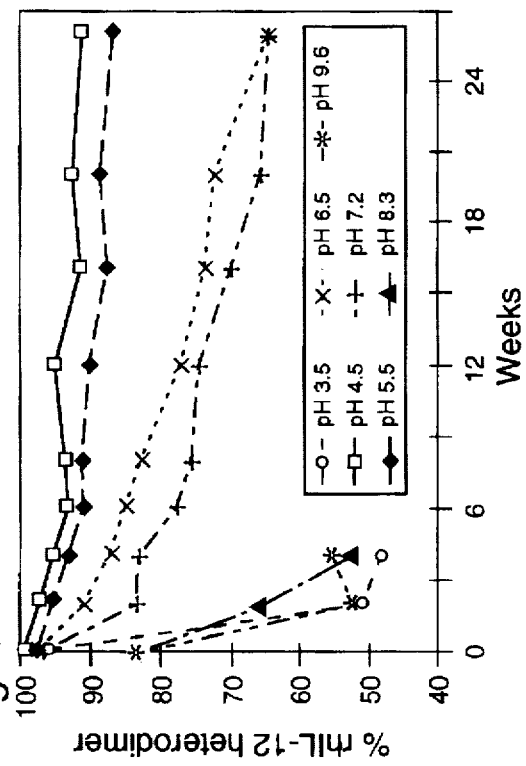
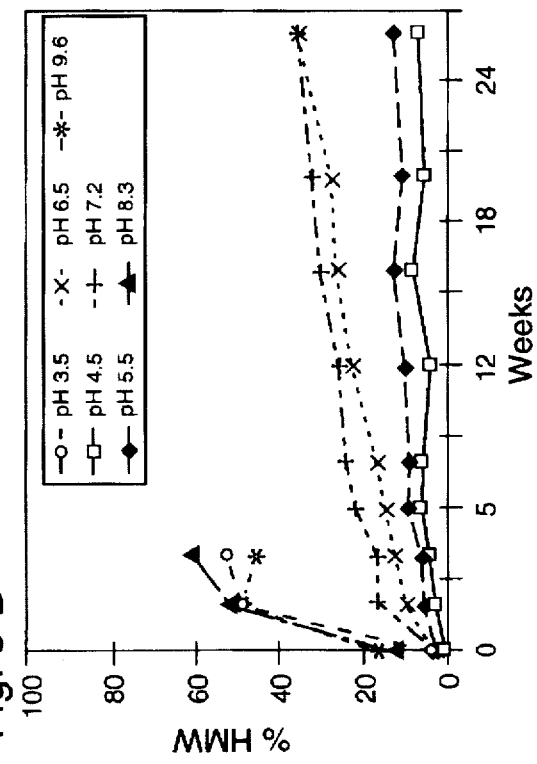
Fig. 3-A
Fig. 3-B
Fig. 3-C 1. pI marker
2. pH 3.5
3. pH 4.5
4. pH 5.5
5. pH 6.5
6. pH 7.2
7. pH 8.3
8. pH 9.6
9. pI marker

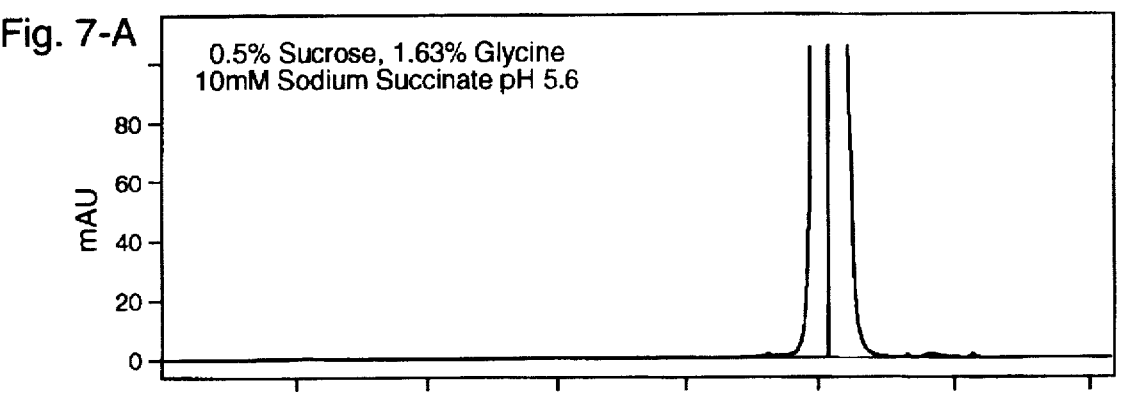
Fig. 7-A
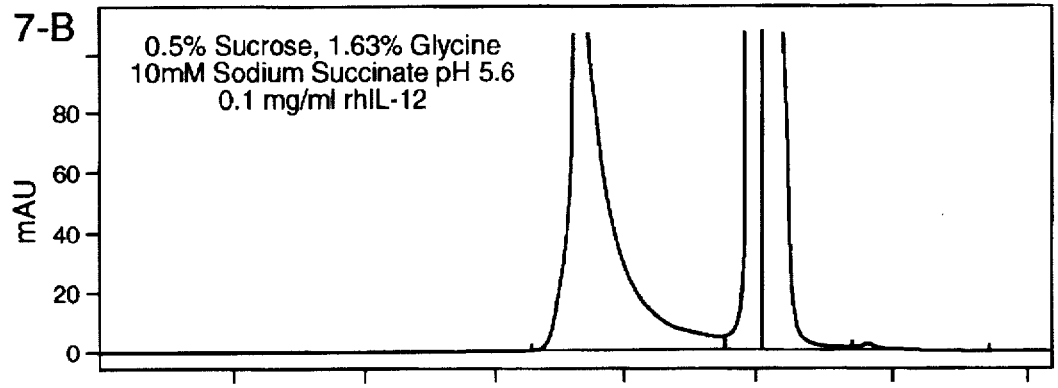
Fig. 7-B
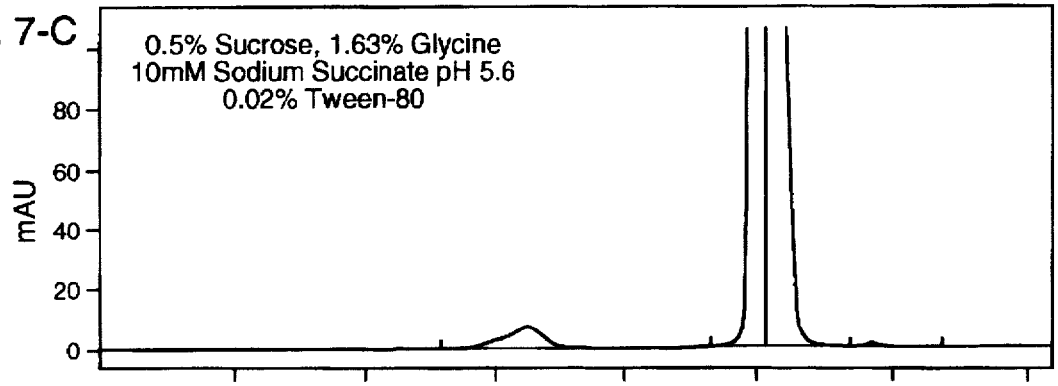
Fig. 7-C
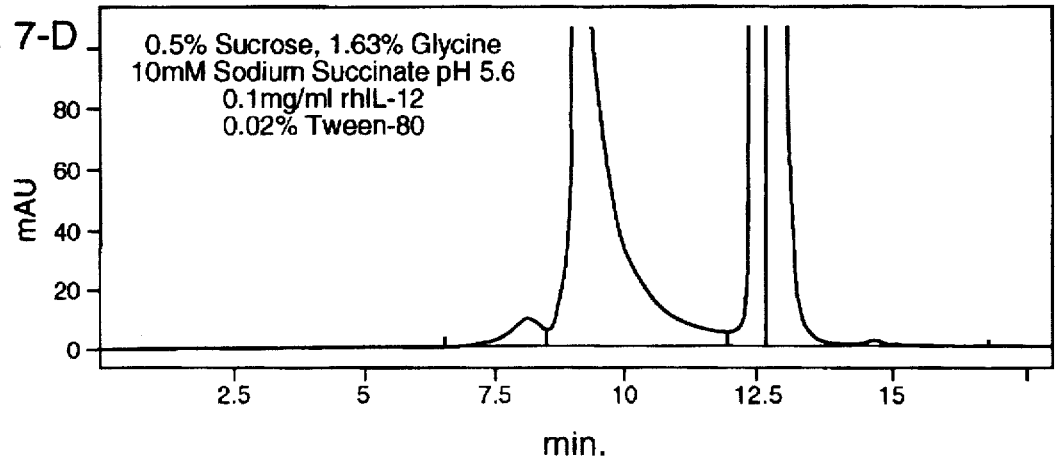
Fig. 7-D

Fig. 9-A
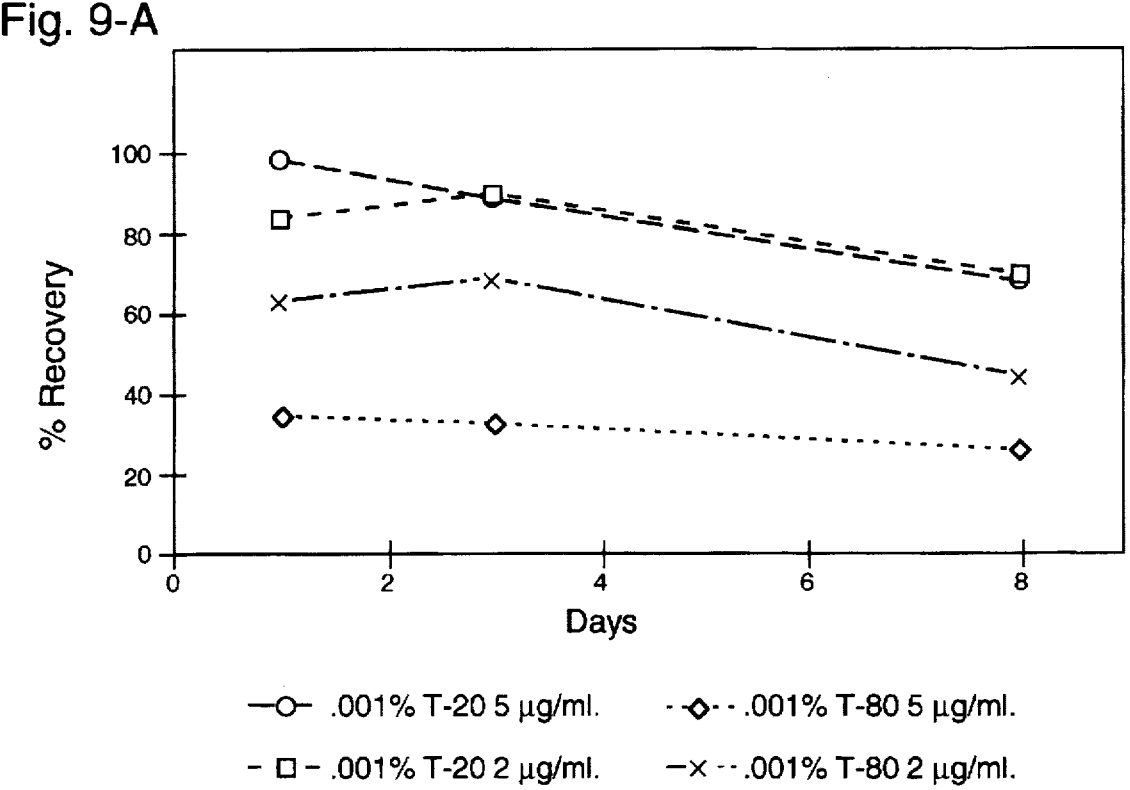
—○— .001% T-20 5 µg/ml.  · · ◇ · · .001% T-80 5 µg/ml.
— □ — .001% T-20 2 µg/ml.  —×— · .001% T-80 2 µg/ml.
Fig. 9-B
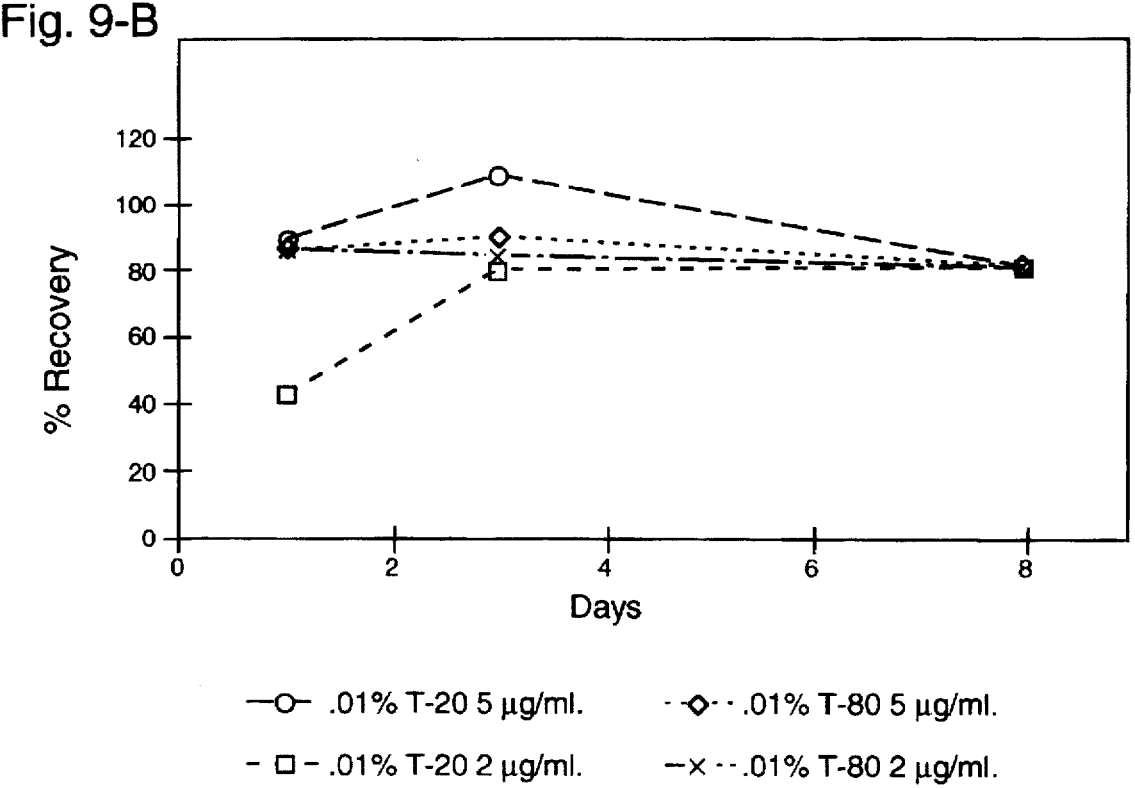
—○— .01% T-20 5 µg/ml.  · · ◇ · · .01% T-80 5 µg/ml.
— □ — .01% T-20 2 µg/ml.  —×— · .01% T-80 2 µg/ml.

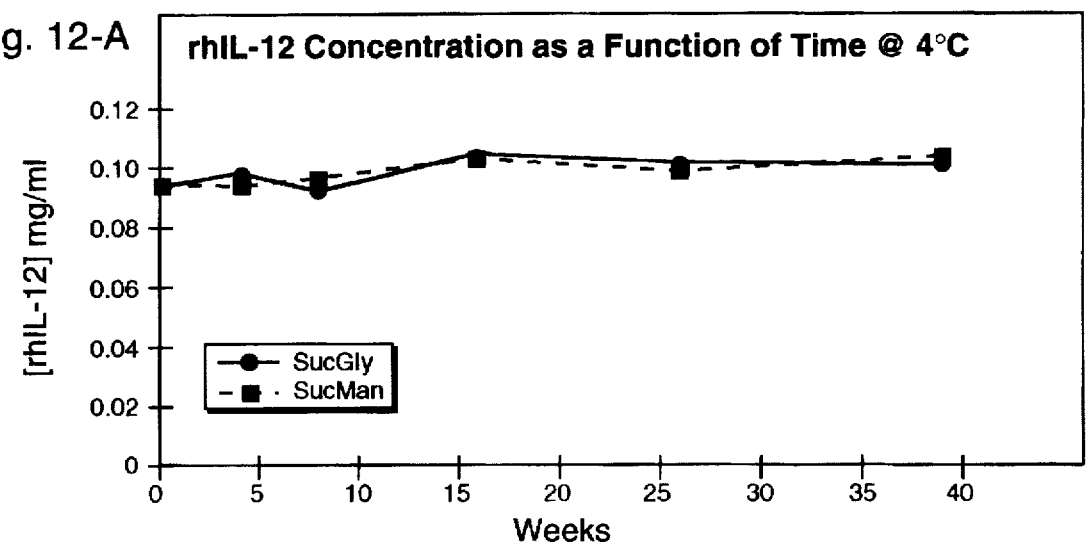
Fig. 12-A
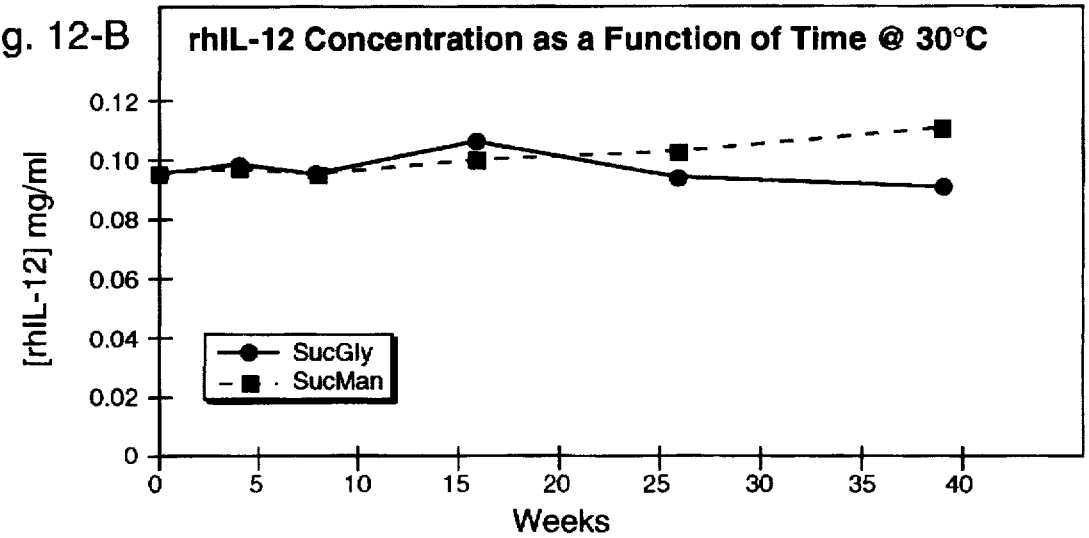
Fig. 12-B
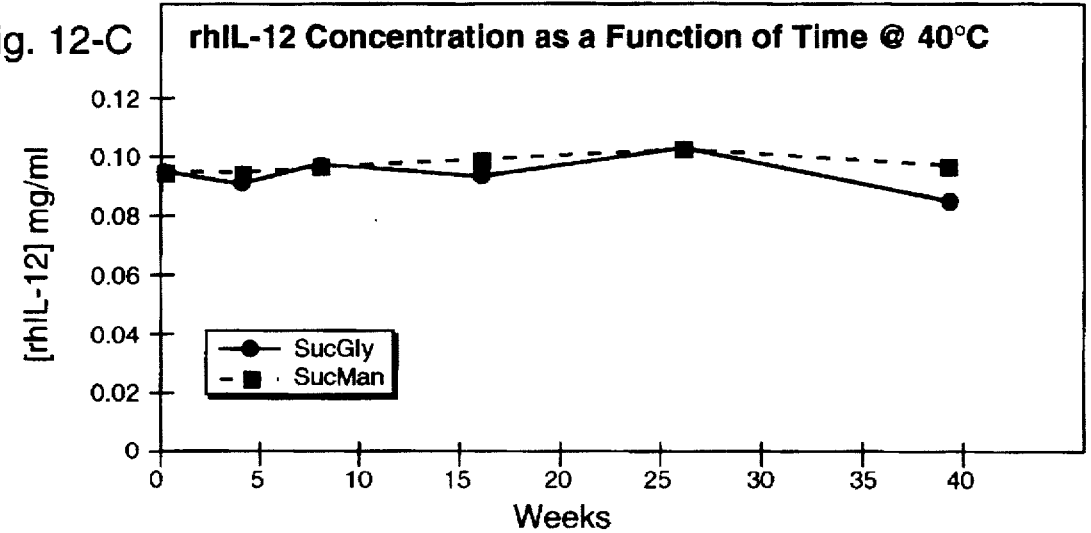
Fig. 12-C

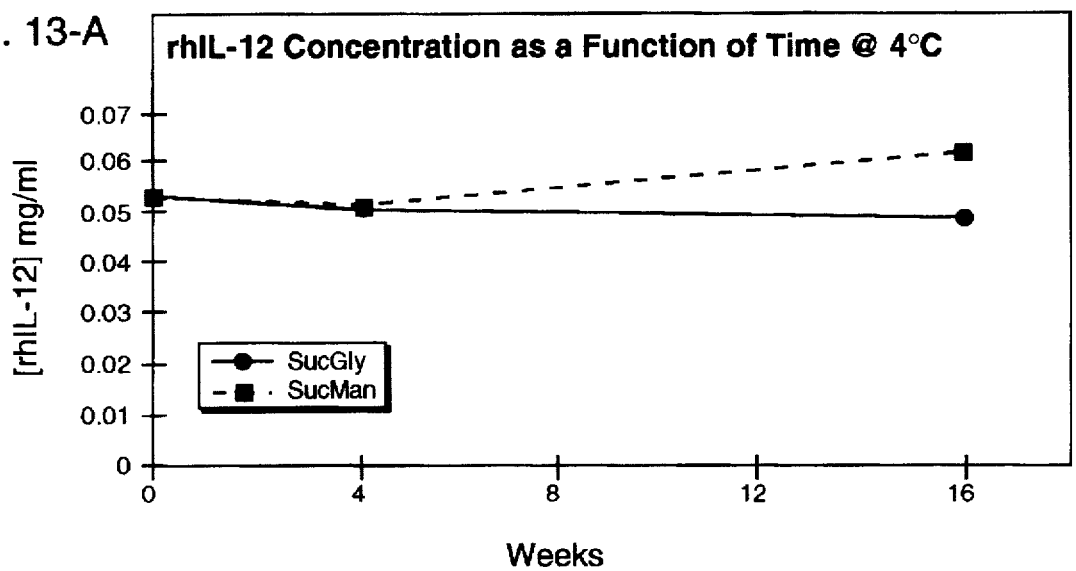
Fig. 13-A
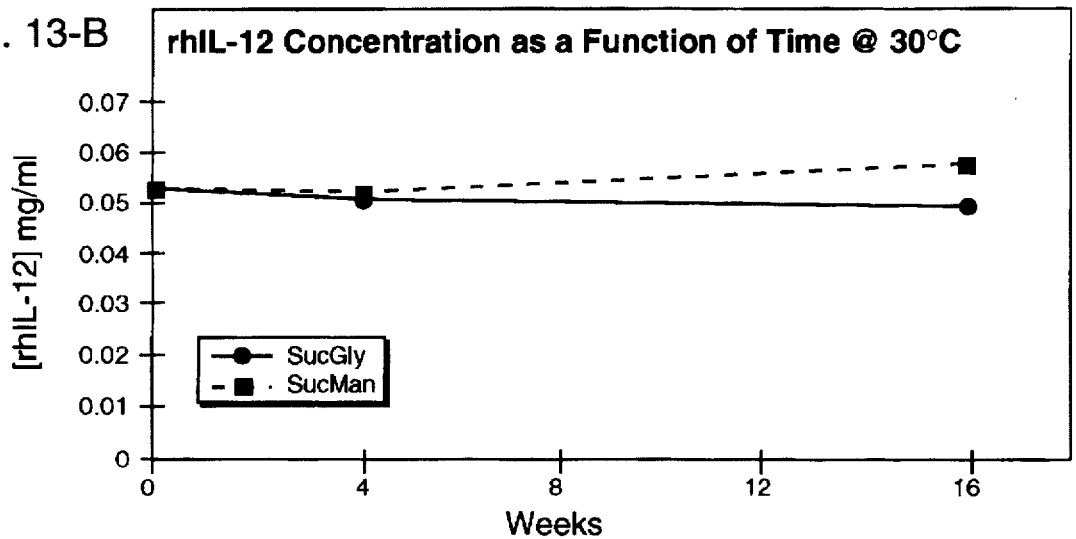
Fig. 13-B
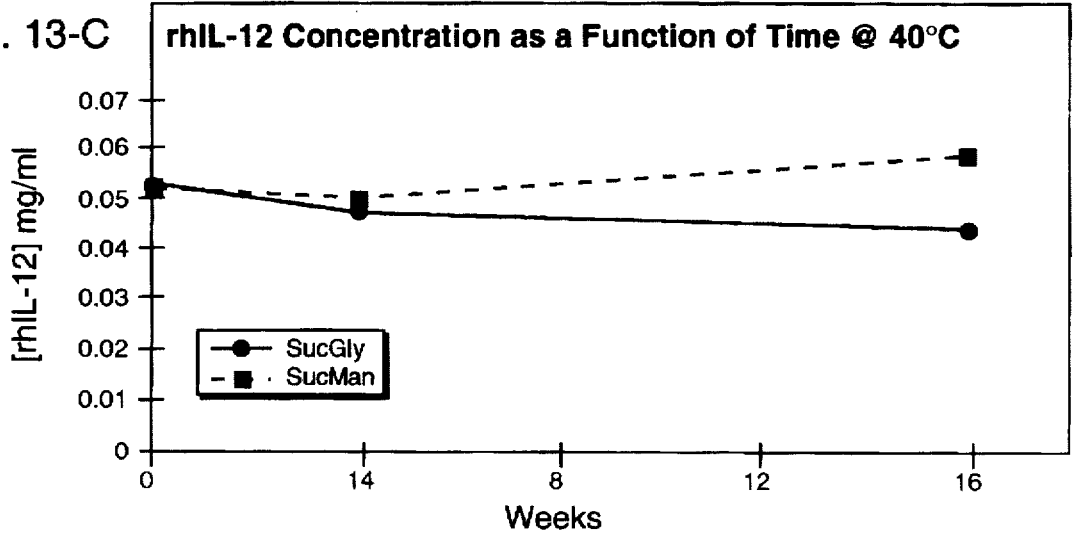
Fig. 13-C

Fig. 14-A
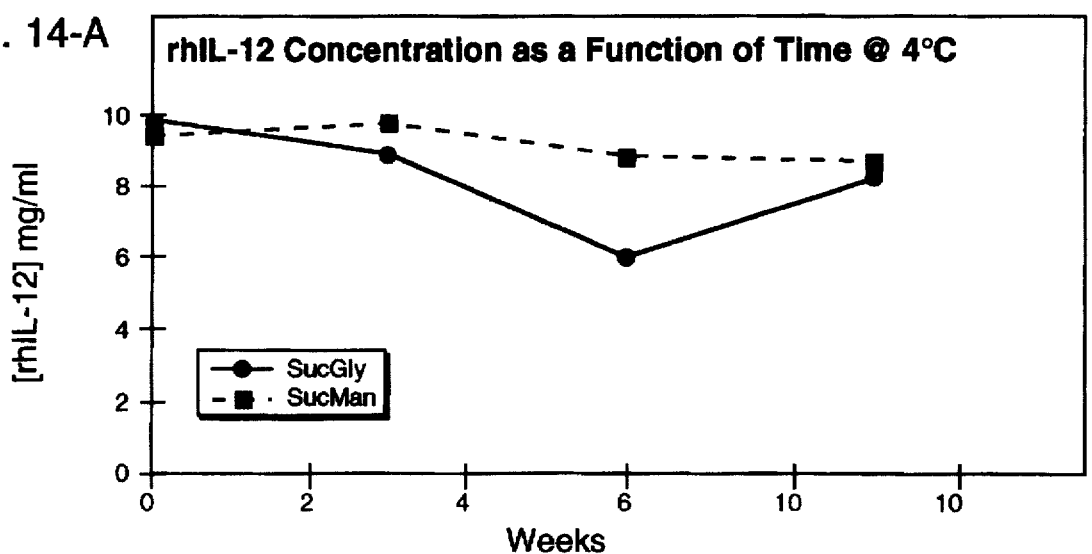
Fig. 14-B
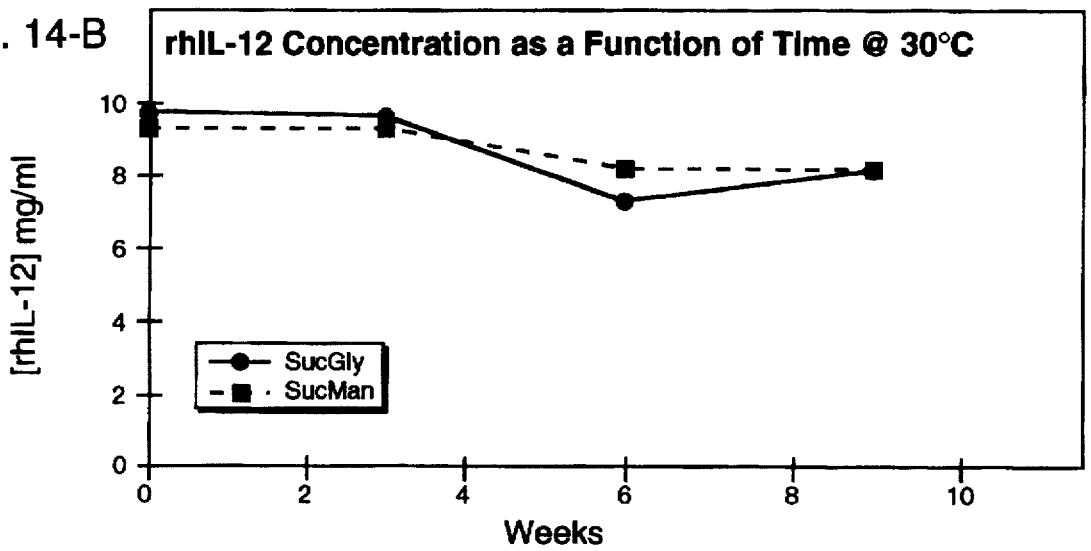
Fig. 14-C
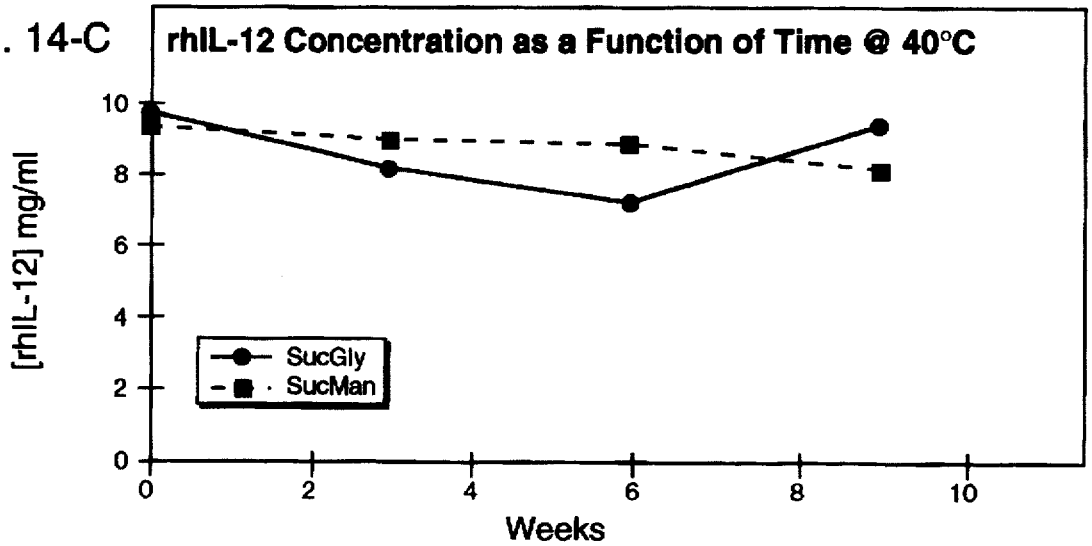

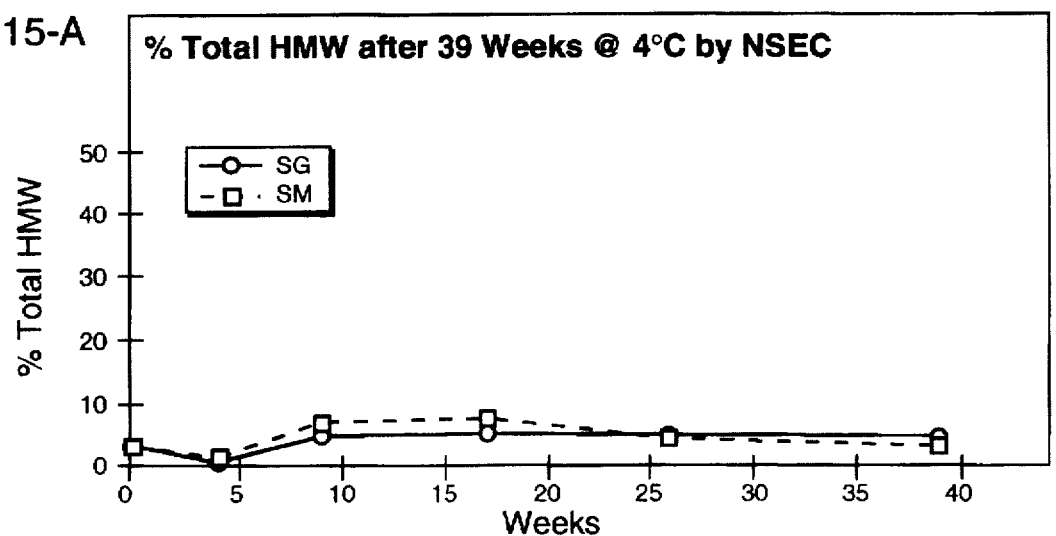
Fig. 15-A
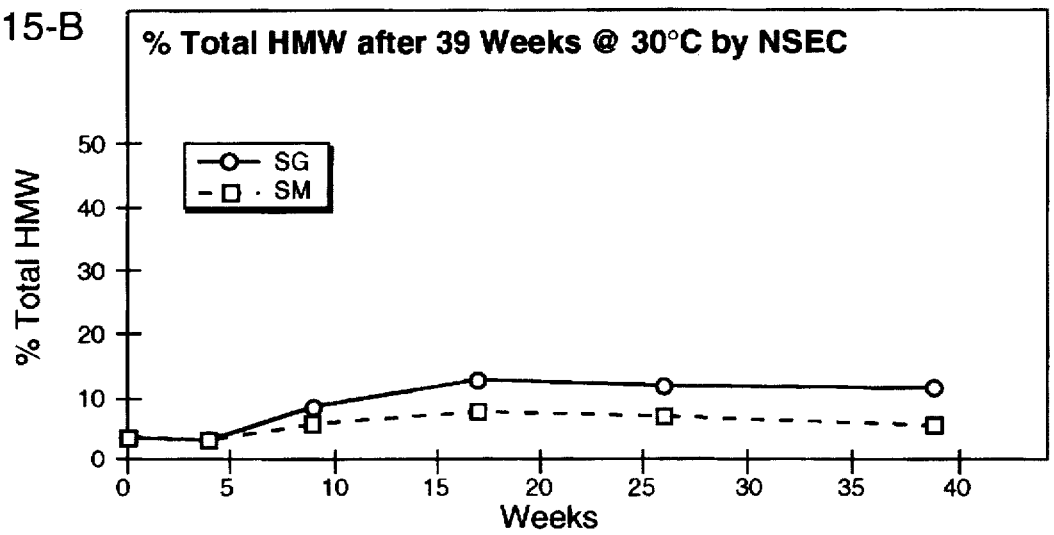
Fig. 15-B
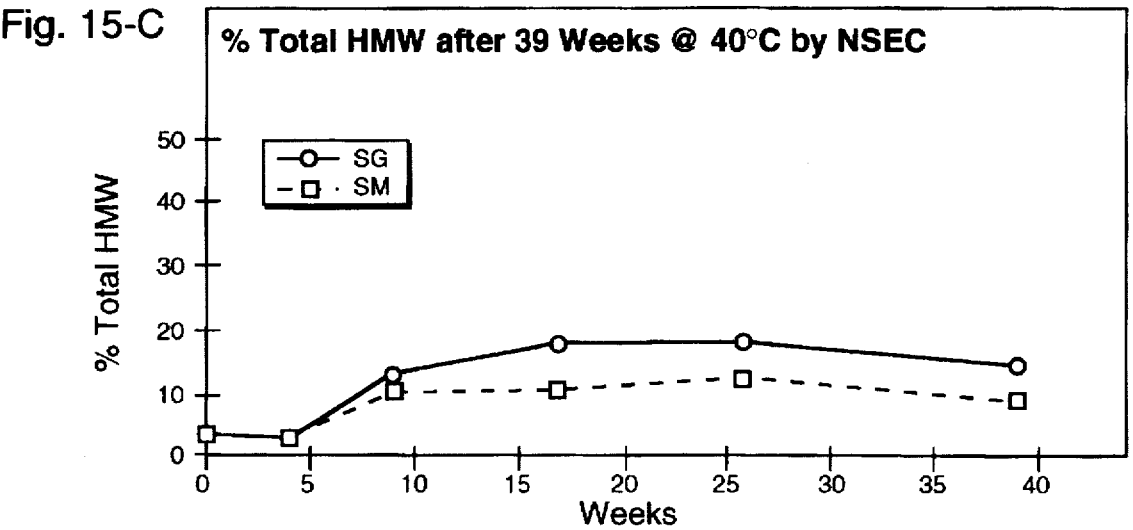
Fig. 15-C

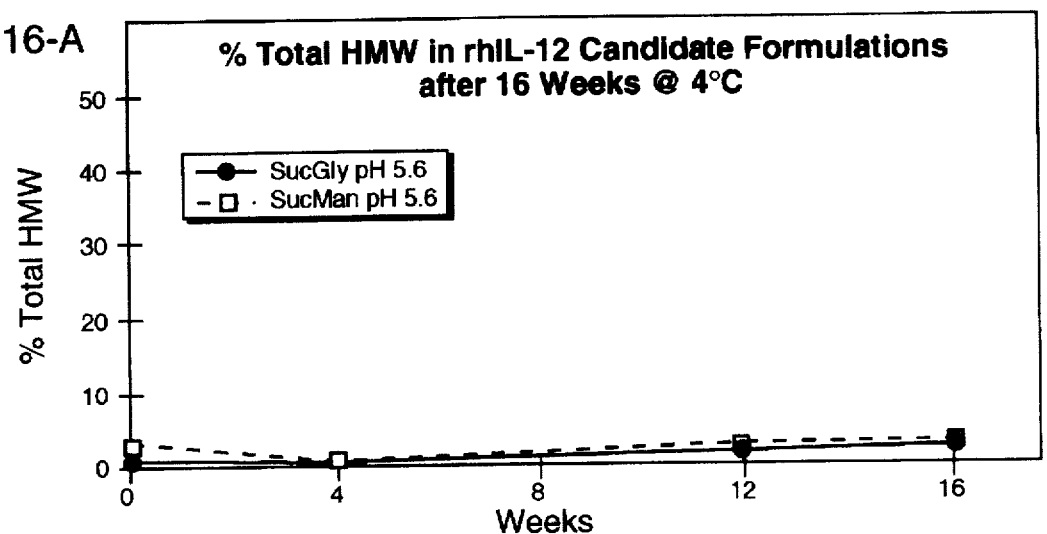
Fig. 16-A
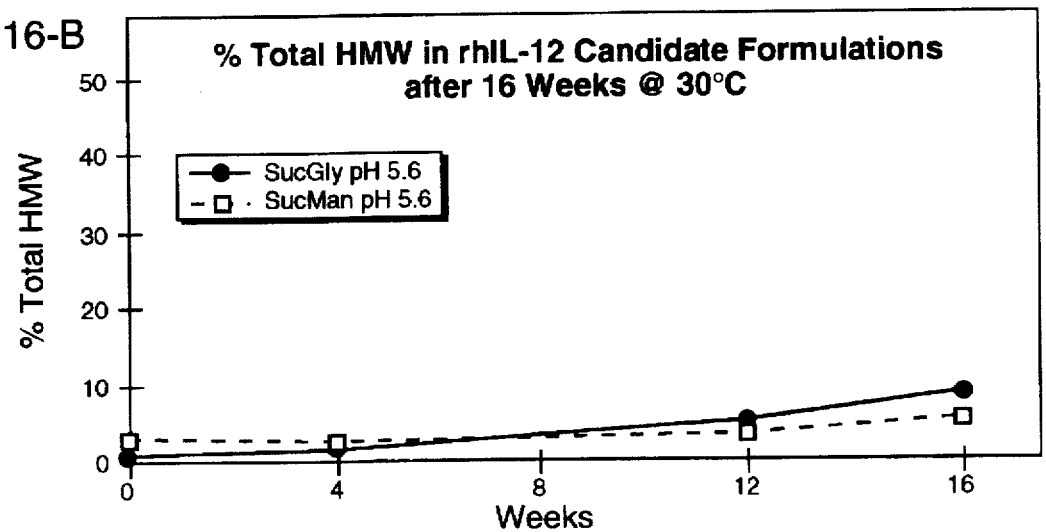
Fig. 16-B
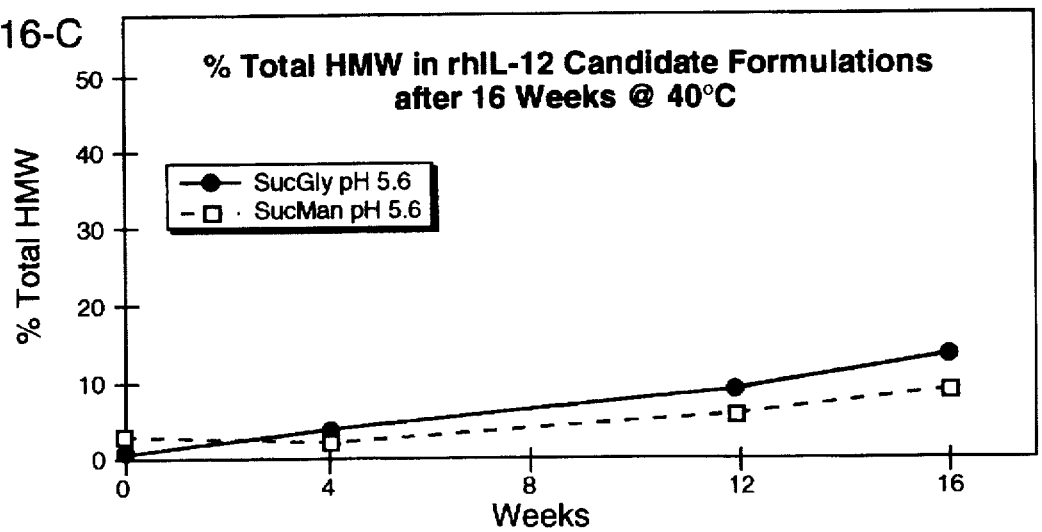
Fig. 16-C

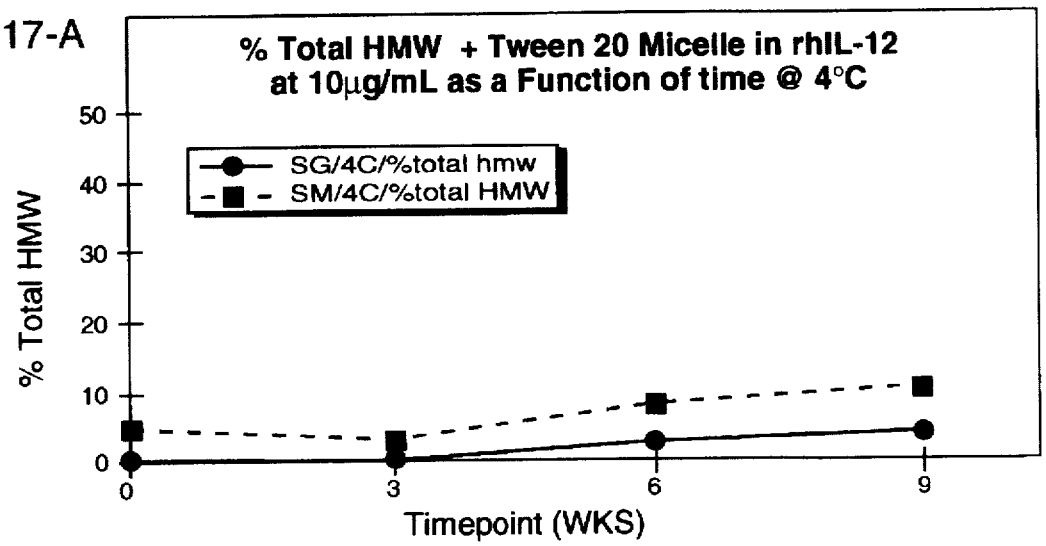
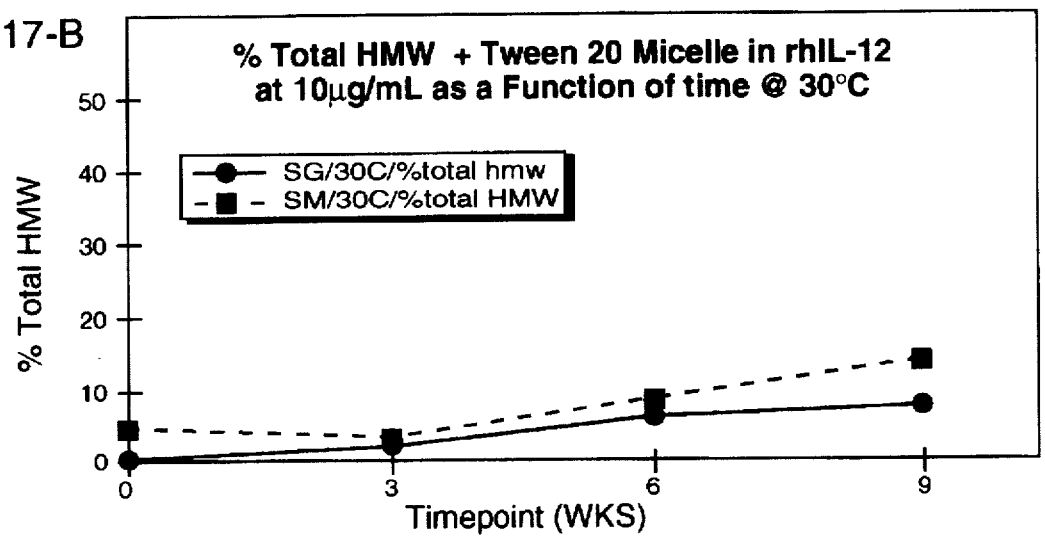
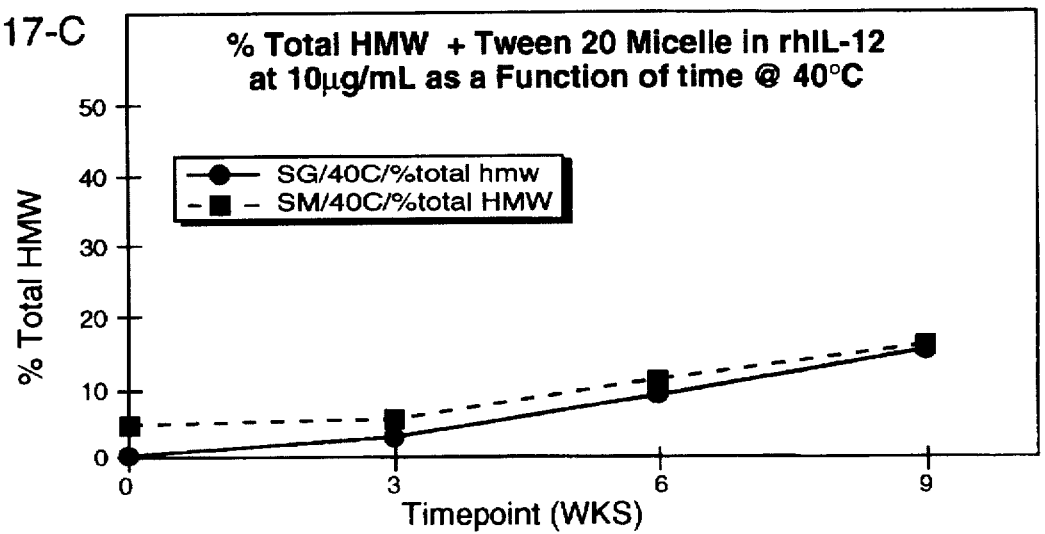

FORMULATIONS FOR IL-12

This application is a continuation of application Ser. No. 08/384,062, filed Feb. 6, 1995 now abandoned.

FIELD OF INVENTION

The present invention relates generally to novel formulations comprising interleukin-12 ("IL-12").

BACKGROUND OF THE INVENTION

IL-12 is a heterodimeric cytokine (comprising an approximately 35 kD subunit ("p35") and an approximately 40 kD subunit ("p40"), which was originally identified as a factor which induces γ-interferon from T cells and natural killer cells, as set forth in PCT/US91/06332, published Apr. 2, 1992, which is incorporated herein by reference. PCT/US91/06332 refers to IL-12 as Natural Killer Cell Stimulating Factor or NKSF. EP 433827, published Jun. 26, 1991 discloses IL-12 as a cytotoxic lymphocyte maturation factor (CLMF). These patent publications also disclose the cloning and expression of IL-12 and its subunits. Thus, through advances in recombinant DNA technology, it has been possible to produce IL-12 protein.

Interleukin-12 also stimulates natural killer cells in vitro by increasing their ability to lyse target cells at a level comparable to that obtained with interferon-α and interleukin-2, well-known activators of natural killer cells' cytotoxic activity. Additional in vitro activities of interleukin-12 which have been identified include induction of T cell proliferation as a co-stimulant; suppression of interleukin-2 induced proliferation of natural killer blasts; suppression of interleukin-2 induced proliferation of T cell receptor-γδ-positive cells; promotion of Th1 T cell differentiation from progenitors; enhancement of Th1, but not Th2 proliferation; enhancement of T cell cytolytic activity; enhancement of cytotoxic lymphocyte generation; enhancement of natural killer and natural killer blast cytolytic activity; ex vivo enhancement of natural killer activity in peripheral blood mononuclear cells of interleukin-2-treated patients; induction of adhesion molecules on natural killer cells; induction of perforin and granzyme B mRNAs in natural killer blasts; induction of interleukin-2 receptor subunits (p55, p75) on natural killer cells; induction of low levels of tumor necrosis factor-α; suppression of IgE synthesis by interferon-γ-dependent and independent mechanisms; modulation of T cell development in fetal thymic organ cultures; and synergy with kit ligand to promote growth of myeloid and B cell progenitors. The known in vivo activities of interleukin-12 include induction of interferon-γ; enhancement of natural killer cell activity in spleen, liver, lungs and peritoneal cavity; enhancement of generation of allo-specific cytotoxic lymphocytes; induction of extramedullary hematopoiesis in mouse spleen; reversible suppression of hematopoiesis in bone marrow; reversible induction of anemia, lymphopenia, and neutropenia in mice; suppression of anti-IgD induced IgE, IgG1, and interleukin-4 expression; increased survival in SCID mice treated with *Toxoplasma gondii*; cure of leishmaniasis in susceptible strains of mice; decreased bioburden in cryptococcoses model; suppression of tumor growth; and promotion of immunity to tumor cells. Interleukin-12 is also induced in vivo in the shwarzman reaction model of septic shock.

It is desirable to have concentrated forms of bulk protein, e.g., IL-12, which, in turn, may be stored and which are suitable for further manufacture of finished dosage forms of protein. Typically, a purification process for a protein results in concentrating the protein. This concentrated protein, also known as bulk protein, may be in a formulation buffer. Bulk protein, typically at a concentration of about 0.1 to at least 20 mg/ml, can then be shipped frozen to a fill/finish facility where it is diluted to an appropriate dosage concentration and placed into dosage vials. These diluted samples can be lyophilized, i.e., freeze-dried. The lyophilized samples may be kept in long-term storage and reconstituted at a later time by adding a suitable administration diluent just prior to patient use.

Protein stability can be affected inter alia by such factors as ionic strength, pH, temperature, repeated cycles of freeze/thaw and exposures to shear forces. Active protein may be lost as a result of physical instabilities, including denaturation and aggregation (both soluble and insoluble aggregate formation), as well as chemical instabilities, including, for example, hydrolysis, deamidation and oxidation, to name just a few. For a general review of stability of protein pharmaceuticals, see, for example, Manning, et al., Pharmaceutical Research 6:903–918 (1989).

While the possible occurrence of protein instabilities is widely appreciated, it is impossible to predict particular instability problems of a particular protein. Any of these instabilities can result in the formation of a protein, protein by-product, or derivative having lowered activity, increased toxicity, and/or increased immunogenicity. Also, IL-12 has a tendency to form soluble high molecular weight aggregates which can interfere with product quality and effectiveness in use. Thus, the safety and efficacy of any pharmaceutical formulation of a protein is dependent upon its stability.

In addition to stability considerations, one generally selects excipients which are or will meet with the approval of various world-wide medical regulatory agencies. The solution should be isotonic and the pH in a physiologically suitable range. The choice and amount of buffer used is important to achieve and maintain the desired pH range.

Ideally, formulations should also be stable for IL-12 bulk storage in high concentration ($\geq 20$ mg/ml, for example) which allows for relatively small volumes for fill/finish at the appropriate dose and also allows for alternate methods of administration which may require high protein concentration, e.g., sub cutaneous administration. Accordingly, there continues to exist a need in the art for methods for monitoring IL-12 protein stability (and maintaining activity levels) during the concentration process and the lyophilization process, as well as providing stable formulations during prolonged storage.

BRIEF SUMMARY OF THE INVENTION

One aspect of the present invention provides novel compositions and methods for providing concentrated preparations of IL-12, useful as drug product. These compositions, either frozen, liquid, or lyophilized (preferably lyophilized), comprise: (a) a protein selected from the group consisting of IL-12, a biologically active fragment of IL-12, a subunit of IL-12, and a multimer of a subunit of IL-12; (b) a polysorbate; (c) a cryoprotectant; (d) a bulking agent; and (e) a buffering agent which maintains the pH of said composition in the range of from about 4.5 to about 7.4.

Preferably, the cryoprotectant is selected from the group consisting of sucrose, maltose, lactose and combinations thereof. Preferably, the cryoprotectant comprises about 0.5 to about 5% of the composition. When sucrose is used, a preferred concentration is from about 0.5 to about 2%, most preferably about 2%. Preferably the bulking agent is selected from the group consisting of mannitol, glycine and combinations thereof. Preferably the bulking agent comprises about 1 to about 5% of the composition. When mannitol is used, a preferred concentration is from about 3 to 5%, most preferably about 4.15%. Combinations of sucrose/mannitol and sucrose/glycine are particularly preferred.

Preferably the polysorbate is selected from the group consisting of polysorbate TWEEN-20 and polysorbate TWEEN-80, most preferably polysorbate TWEEN-20. In certain embodiments, the polysorbate is present at a concentration of about 0.001 to 0.1%, preferably at a concentration of about 0.001 to 0.1%, most preferably at a concentration of about 0.02%. A plurality of polysorbates may also be used.

In preferred embodiments, the buffering agent maintains the pH of said composition in the range of from about 5.2 to about 7.4, most preferably at about 5.6. Preferred buffering agents are selected from the group consisting of succinate, histidine, phosphate, Tris, and diethanolamine, with succinate (particularly the sodium and potassium salts thereof) being most preferred.

Preferably the protein is present at a concentration of about 1 µg/ml to about 20 mg/ml, more preferably at about 1 to about 1000 µg/ml, most preferably at a concentration of about 5 to about 500 µg/ml.

Particularly preferred embodiments of the invention comprise about 5 to about 500 µg/ml IL-12, about 2% sucrose, about 4.15% mannitol, about 10 mM sodium succinate, and about 0.02% polysorbate TWEEN-20, and having a pH of about 5.6.

BRIEF DESCRIPTION OF THE FIGURES

FIG. 2 shows quantitative SDS-PAGE data collected up to 12 weeks of storage at 30° C. at various pHs.

FIG. 3 shows a Size Exclusion Chromatography (SEC) analysis of rhIL-12 at a variety of pHs after storage for 26 weeks at 30° C.

FIG. 7 shows SEC traces from a 2×2 multi-variable matrix experiment and demonstrates that a tween-80 micelle co-elutes with the HMW aggregate.

FIG. 9 shows the results of an adsorption study comparing tween-20 with tween-80.

FIGS. 12–14 are graphs showing the progression of rhIL-12 concentration over time for test formulations containing 0.1 mg/ml, 0.05 mg/ml and 0.01 mg/ml rhIL-12, respectively.

FIGS. 15–17 are graphs showing the progression of HMW aggregate content over time test formulations containing 0.1 mg/ml, 0.05 mg/ml and 0.01 mg/ml rhIL-12, respectively.

DETAILED DESCRIPTION OF THE INVENTION

Figure 1:
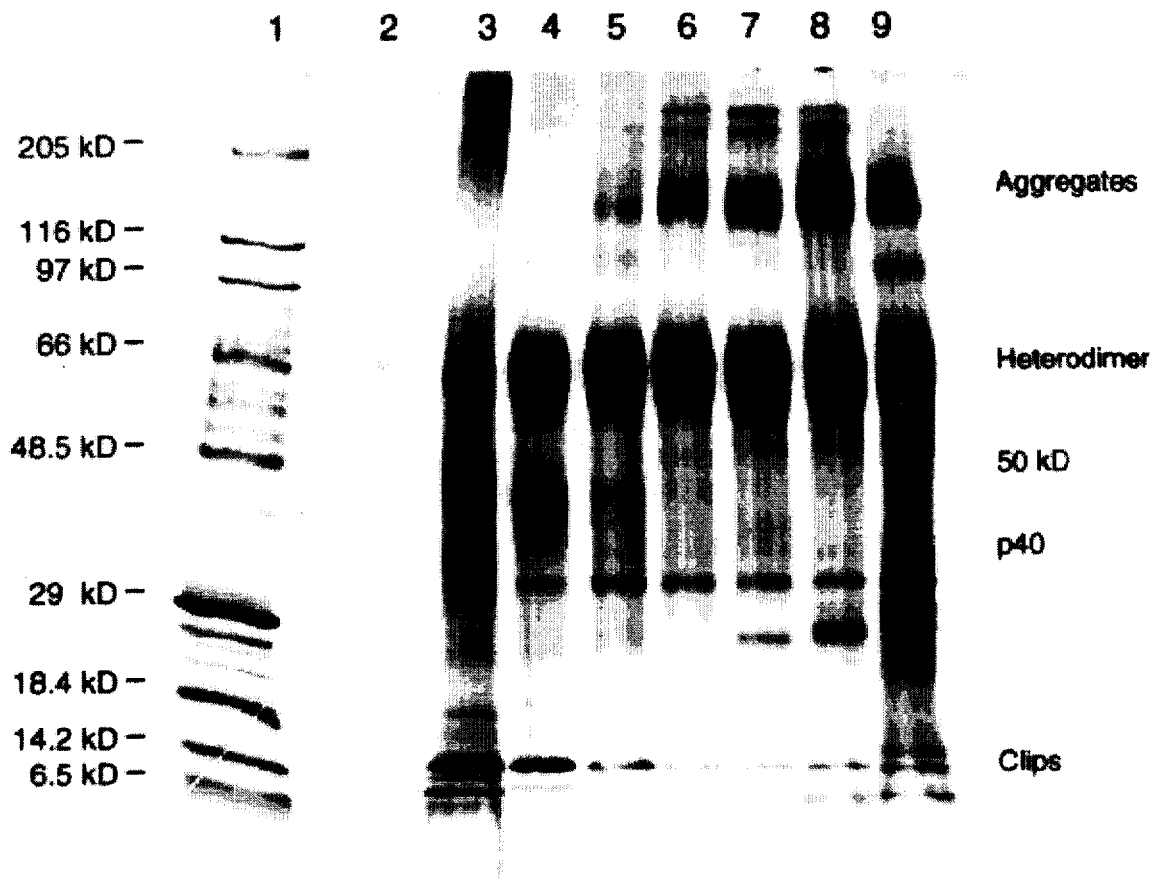
FIG. 1 shows the results of SDS-PAGE analysis of rhIL-12 at a variety of pH's for 16 weeks at 30° C.

As used herein, the terms lyophilization, lyophilized, and freeze-dried include but are not limited to processes including "freezing" a solution followed by "drying", optionally in vacuo (although vaccum is not preferred). As used herein, the term "bulking agent" comprises agents which provide good lyophilized cake properties, which help the protein overcome various stresses (shear/freezing for example) associated with the lyophilization process, and which help to maintain protein activity levels. Exemplary bulking agents include, but are not limited to, glycine, mannitol, $MgCl_2$, $CaCl_2$, NaCl, and the like. These agents contribute to the tonicity of the formulations. Cryoprotectants also contribute to the tonicity. The term "cryoprotectants" generally includes agents which provide stability to the protein from freezing-induced stresses; however, the term also includes agents that provide stability, e.g., to bulk drug formulations during storage from non-freezing-induced stresses. Exemplary cryoprotectants include polyols, and include saccharides such as sucrose and mannitol, as well as including surfactants such as polysorbate, or polyethyleneglycol, and the like. The term "cryoprotectant" includes agents that provide stability to the protein during water removal from the system during the drying process, presumably by maintaining the proper conformation of the protein through hydrogen bonding. Cryoprotectants can also have lyoprotectant effects; therefore, the terms "cryoprotectant" and "lyoprotectant" are used interchangeably herein.

The term "buffering agent" encompasses those agents which maintain the solution pH in an acceptable range prior to lyophilization and may include succinate (sodium or phosphate), histidine, phosphate (sodium or potassium), Tris (tris (hydroxymethyl) aminomethane), diethanolamine, and the like. The upper concentration limits are generally higher for "bulk" protein than for "dosage" protein forms as is readily appreciated by one skilled in the art. For example, while buffer concentrations can range from several millimolar up to the upper limit of their solubility, e.g., succinate could be as high as 200 mM, one skilled in the art would also take into consideration achieving/maintaining an appropriate physiologically suitable concentration. Percentages are weight/weight when referring to solids and weight/volume when referring to liquids. The term "isotonic," 300±50 mOsM, is meant to be a measure of osmolality of the protein solution prior to lyophilization; reconstitution is typically with water for injection (WFI). Maintaining physiological osmolality is important for the dosage formulations. However, for bulk formulations, much higher concentrations can be effectively utilized as long as the solution is made isotonic prior to use. The term "excipients" includes pharmaceutically acceptable reagents to provide good lyophilized cake properties (bulking agents) as well as provide lyoprotection and cryoprotection of the protein, maintenance of pH, and proper conformation of the protein during storage so that substantial retention of biological activity (protein stability) is maintained. Preferably, the combined concentration of the excipients provides a combined osmolality of about 250 to about 350 milliosmol (mOsm) per kg, more preferably about 300 mOsm/kg.

In accordance with the present invention, therefore, native IL-12 is a heterodimeric glycoprotein comprised of two covalently linked subunits, one of said subunits having a molecular weight of about 40 kD, and the other subunit having a molecular weight of about 35 kD. Any form of IL-12 may be used to practice the invention. For example, IL-12 may be in the form of the heterodimer comprised of a 40 kD subunit disulfide-bonded to a 35 kD subunit. When IL-12 is a heterodimer, the 40 kD subunit has substantial homology to the 40 kD subunit of human IL-12 as set forth in PCT/US91/06332 or EP 433827 and is disulfide bonded to a 35 kD subunit having substantial homology to the 35 kD subunit of human IL-12 as set forth in those patent publications. "Substantial homology" means greater than 75% homology at the amino acid level, while retaining the desired biological function. Another form of IL-12 which may be used in the present invention is an IL-12 subunit. Such an IL-12 40 kD subunit has substantial homology to the human IL-12 40 kD subunit, and such an IL-12 35 kD subunit has substantial homology to the human IL-12 35 kD subunit. Fragments of the IL-12 subunits that retain IL-12 biological activity are also be useful for making formulations in accordance with the present invention. Multimers, such as homodimers, of IL-12 subunits may also be used.

For use in the present invention, it is preferable to produce IL-12 recombinantly, through expression of DNA sequences encoding one or both of the IL-12 subunits in a suitable transformed host cell. For example, using known methods the DNA sequences encoding human IL-12 may be linked to an expression vector such as pED (Kaufman et al., Nucleic Acids Res. 19, 4484–4490(1991)). In such an expression vector, sequences which optimize translation such as CCACC (Kozak, M., Nucleic Acids Res. 12, 857–871 (1984)) may be added 5' to the initiation codon using known methods. The expression vector containing the IL-12 subunits may then be transformed into a host cell, and protein expression may be induced and maximized, to produce heterodimeric human IL-12. For production of heterodimeric IL-12, the DNA sequences encoding the IL-12 subunits may be present on different expression plasmids or present in tandem on a single expression plasmid.

When a subunit or fragment of IL-12 is used to practice the present invention, it may also be produced recombinantly using known methods. For example, the DNA sequence encoding the human IL-12 40 kD subunit may be linked to an expression vector, transformed into a host cell, and expression induced and maximized to produce the human IL-12 40 kD subunit. Similarly, the DNA sequences encoding the human IL-12 35 kD subunit may be linked to an expression vector, transformed into a host cell, and expression induced and maximized to produce the corresponding protein. Of course, degenerate DNA sequences encoding the IL-12 subunits may also be employed to produce IL-12 for use in the present invention, as can DNA sequences encoding allelic variants of the IL-12 subunits.

Any suitable expression vector may be employed to produce IL-12 for use in the present invention. For mammalian expression, numerous expression vectors are known in addition to the pED vector mentioned above, such as pEF-BOS (Mizushima et al., Nucleic Acids Res. 18, 5322 (1990)); pXM, pJL3 and pJl4 (Gough et al., EMBO J. 4, 645–653 (1985)); and pMT2 (derived from pMT2-VWF, A.T.C.C. #67122; see PCT/US87/00033). Suitable expression vectors for use in yeast, insect, and bacterial cells are also known. Construction and use of such expression vectors is well within the level of skill in the art.

Suitable host cells for recombinant production of IL-12 useful in the present invention include, for example, mammalian cells such as Chinese hamster ovary (CHO) cells, monkey COS cells, mouse 3T3 cells, mouse L cells, myeloma cells such as NSO (Galfre and Milstein, Methods in Enzymology 73, 3–46 (1981)), baby hamster kidney cells, and the like. IL-12 may also be produced by transformation of yeast, insect, and bacterial cells with DNA sequences encoding the IL-12 subunits, induction and amplification of protein expression, using known methods.

Recombinantly produced IL-12 can be purified from culture medium or cell extracts by conventional purification techniques. Culture medium or cell extracts containing IL-12 may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups.

The purification of IL-12 from culture supernatant may also include one or more column steps over such affinity resins as lectin-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify IL-12 for use in the present methods and compositions. Some or all of the foregoing purification steps, in various combinations, can be employed to provide a substantially homogeneous isolated recombinant protein. Purification of IL-12 subunits or fragments for use in the present invention may differ from the optimal protocol for purification of the heterodimeric protein.

Preferably, when human IL-12 is produced recombinantly as set forth above, it may be purified by the following method. The cells in which the human IL-12 has been made may be removed from the conditioned medium by filtration, and the conditioned medium is loaded onto Q-Sepharose FastFlow™ (available from Pharmacia) or an equivalent anion exchange medium, which has been equilibrated in 10–30 mM Tris-HCl, pH 7.8–8.3. The column is then washed extensively with the same buffer followed by a wash with 30–45 mM histidine, pH 5.1–5.8, followed by a wash with the original equilibration buffer. The recombinant human IL-12 is eluted from the column with a buffer containing 20–50 mM Tris-HCl, pH 7.8–8.5, and 0.15 to 0.50M NaCl. the eluted material is loaded onto CM-Sepharose FastFlow™ (available from Pharmacia) or equivalent cation exchange medium which has been equilibrated in 20–50 mM MES, pH 5.7–6.4, and washed extensively with the same buffer. The column is washed with a buffer containing 20–40 mM sodium phosphate, pH 6.8–7.5 and 0.2–0.5M NaCl. The eluted material is concentrated using an Amicon™S1Y30 or equivalent spiral cartridge membrane which has been washed and equilibrated in the elution buffer used in the CM-Sepharose FastFlow™ column. The material is concentrated to approximately 5% of the column volume of the final chromatographic step, which is further purified via size exclusion using S200 Sephacryl™ (available from Pharmacia) or an equivalent size exclusion resin. The size exclusion column is equilibrated and eluted with phosphate buffered saline, pH 7.2–7.6, and the recombinant human IL-12 peak is collected and filtered for use in the method of the invention. Those of skill in the art of protein purification may use alternative purification methods to obtain recombinantly-produced human IL-12 for use in the method of the invention.

IL-12 may be purified from culture medium or extracts of cells which naturally produce the protein and used in the present invention. Exemplary purification schemes for naturally produced IL-12 are set forth in PCT/US91/06332 and in EP 433827.

The following examples illustrate practice of the invention. These examples are for illustrative purposes only and are not intended in any way to limit the scope of the invention claimed.

EXAMPLE 1

Examination of Effect of pH

The effects of pH on the stability and solubility of recombinant human IL-12 (rhIL-12) was examined in a six month stability study. rhIL-12 at a concentration of 1.2 mg/ml was dialyzed into seven buffer ranging in pH from 3.5 to 9.6 (pH 3.5, NaCitrate; pH 4.5, NaGlutamate; pH 5.5, NaSuccinate; pH 6.5, Histidine; pH 7.2, NaPhosphate; pH 8.3, Tris; pH 9.6, glycine). Samples were aseptically vialed and then stored at −80° C., 4° C., 30° C., 40° C. and 50° C. Samples were periodically removed from storage to be analyzed by SEC-HPLC, SDS-PAGE, IEF and RP-HPLC.

FIG. 1 shows the results of SDS-PAGE analysis of rhIL-12 at a variety of pH's for 16 weeks at 30° C. An ISS 3-27% Sepragel was run at constant current with Laemli buffer using a 4.5% acrylamide stack. The gel was silver stained using a Daiichi Silver Stain II kit.

FIG. 2 shows quantitative SDS-PAGE data collected up to 12 weeks of storage at 30° C. at various pHs. Gels were coomasie stained and scanned using a Pharnacia LKB gel scanner. This provided a means to correlate the gels with Size Exclusion Chromatography.

FIG. 3 shows a Size Exclusion Chromatography (SEC) analysis of rhIL-12 at a variety of pHs after storage for 26 weeks at 30° C. A Tosohaas 7.6×300 mm TSK3000swxl column was run isocratically at 0.9 ml/min for 18 minutes using a 20 mM $NaH_2PO_4$, 350 mM NaCl, pH 7.0 running buffer and a 10 µg load. The method was run on a Hewlett Packard 1090 HPLC.

Figure 4:
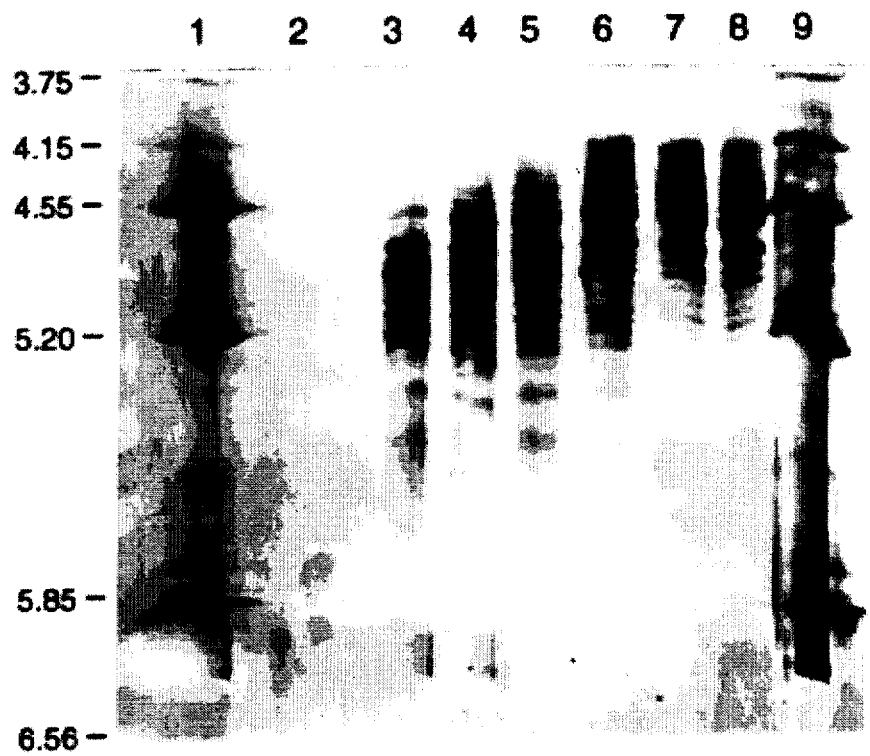
FIG. 4 shows the results of isoelectric focusing of rhIL-12 at a variety of pHs after storage for 16 weeks at 30° C.

FIG. 4 shows the results of isoelectric focusing of rhIL-12 at a variety of pHs after storage for 16 weeks at 30° C. A Pharmacia PAGplate (pI 4.0 to pI 6.5) was prefocused at 1000V, 15 mA, 15 W with 0.5M acetic acid (anode) and 0.5M NaOH (cathode). 5 µg of each sample was loaded using a sample applicator strip. The gel was run at 1000V, 15 mA, 15 W for 2.5 hours, fixed in 20% TCA in EtOH for 45 minutes and then silver stained using the Daiichi Silver Stain II kit.

Figure 5:
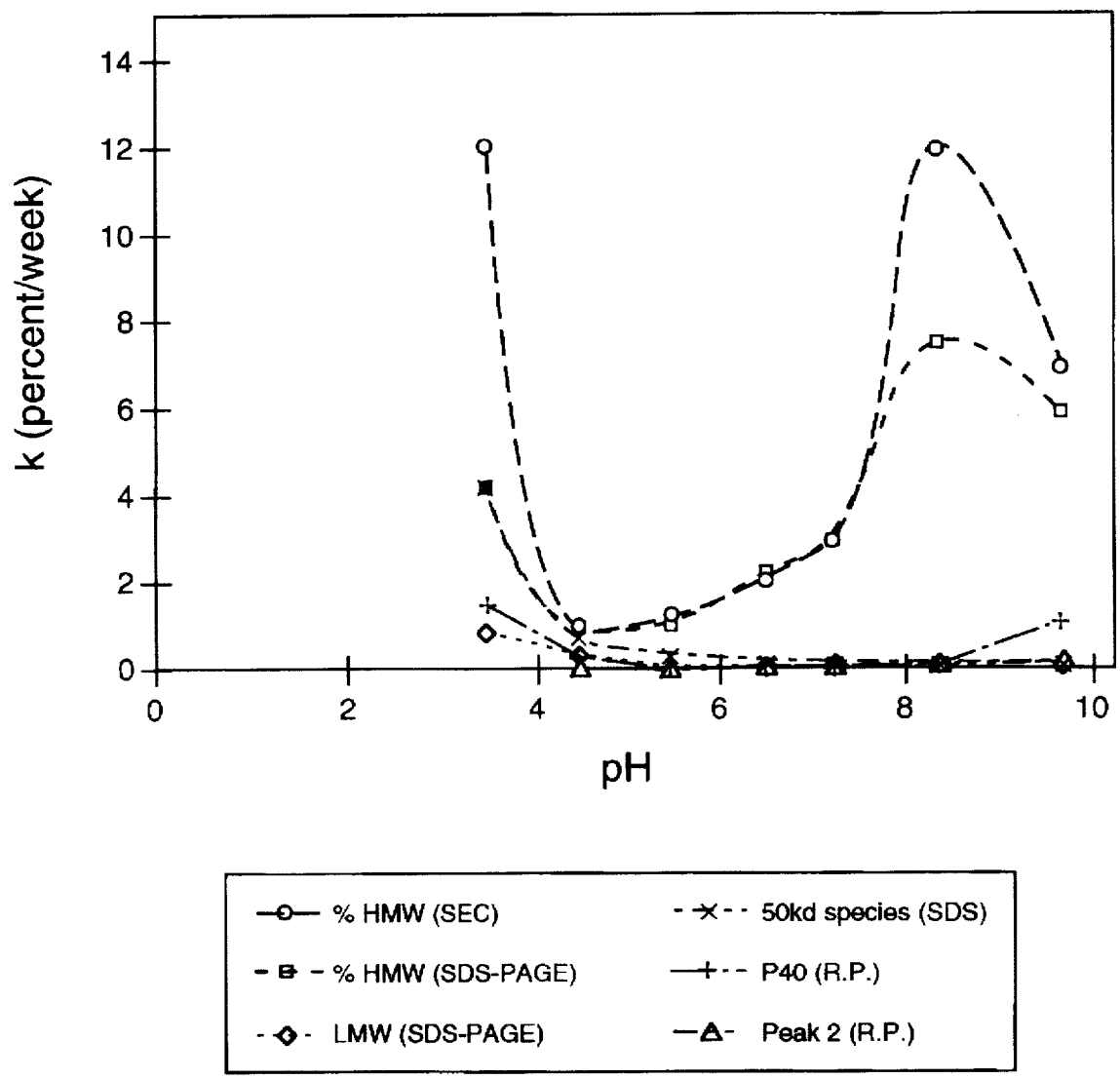
FIG. 5 shows a plot of a fitted line representing the rate (k), which can be thought of as percent loss (rhIL-12 heterodimer) or gain (high molecular weight (HMW) aggregate) per week of storage.

FIG. 5 shows a plot of the rates of generation of various degradation products as a function of pH. This data is based on FIGS. 1–4. The data is summarized in Table I below:

TABLE I

| Instability | Preferable pH Range |
|---|---|
| aggregation via SEC-HPLC | pH 4.5±5.5 |
| aggregation via SDS-PAGE | pH 4.5±5.5 |
| generation of p40 subunit | pH 5.5±8.3 |
| generation of clips via SDS-PAGE | pH ˄ 5.5 |
| charge changes via IEF* | pH 4.5±6.5 |
| generation of 50kD species | pH ˄ 5.5 |

*not included in FIG. 5; data presented in FIG. 4.

Focusing on the 30° C. data set, a number of conclusions can be drawn: (1) Aggregation is minimized at pH 4.5 to 5.5 as observed both by SEC-HPLC and SDS-PAGE analysis. (2) Dissociation of the heterodimer is demonstrated by increased levels of p40 subunit as shown by reversed-phase HPLC and SDS-PAGE; this is minimized at pH 5.5–8.3. (3) Generation of clipped forms is minimized at pH≧5.5 as shown by RP-HPLC and SDS-PAGE, thus avoiding acid-catalyzed hydrolysis. (4) Generation of a 50 kD species is minimized at pH≧5.5. (5) Charge changes observed by IEF gel analysis shows the most stability at pH 4.5–5.5. At basic pH, the samples migrate toward the anode, potentially indicative of deamidation. Based on these results, the most stable pH is approximately 5.5.

EXAMPLE 2

Examination of Effect of Cryoprotectants and Bulking Agents

Several cryoprotectant and bulking excipients were examined for their freeze drying properties. Cryoprotectants examined included glucose, sucrose, maltose, trehalose, fructose and lactose. Bulking agents examined included glycine, mannitol and sorbitol. After differential scanning calorimetry studies (data not shown) six combinations of a cryoprotectant and a bulking agent were selected for further study: sucrose/mannitol, maltose/mannitol, lactose/mannitol, sucrose/glycine, maltose/glycine and glucose/glycine.

Figure 6:
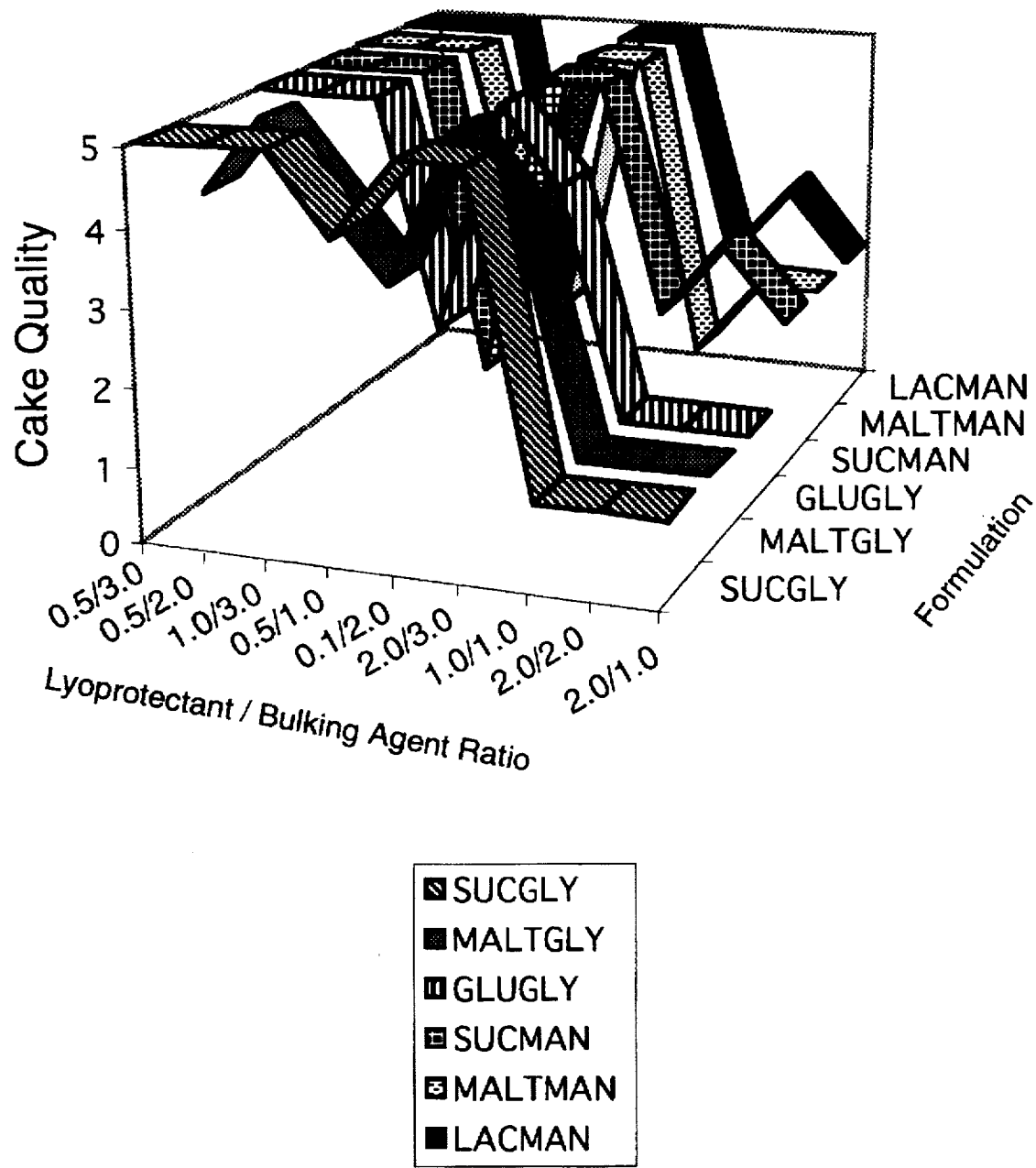
FIG. 6 is a graph comparing the cake quality of rhIL-12 formulations containing different combinations of cryoprotectants and bulking agents.

The six combinations of excipients were combined in nine ratios and freeze-dried using a gentle lyophilization cycle. Each sample contained 0.5 mg/ml rhIL-12 and 10 mM succinate, pH 5.6 (1 ml fill in a 5 ml vial). Cake quality was judged from 1 (worst) to 5 (best). The results are shown in FIG. 6.

The freeze-dried vials prepared as described above were reconstituted and examined for the level of HMW aggregate. In addition, osmolalities were calculated for each of the combinations. The data are reported in Table II.

TABLE II

Top value = cake quality (5 is best, 1 is worst)
Middle value = calculated osmolality (mOsm/kg)
Bottom value = percent HMW aggregate after lyophilization and reconstitution TABLE II-continued

| excipient pairing | .5/3 | .5/2 | 1/3 | .5/1 | 1/2 | 2/3 | 1/1 | 2/2 | 2/1 |
|---|---|---|---|---|---|---|---|---|---|
| sucrose/ glycine | 5 522 0.76 | 5 354 0.70 | 5 537 0.89 | 4 185 0.68 | 5 369 0.95 | 5 567 0.95 | 1 200 1.02 | 1 399 1.03 | 1 230 0.94 |
| maltose/ glycine | 4 522 0.79 | 5 354 0.66 | 4 537 0.88 | 3 185 0.45 | 5 369 0.69 | 4 567 0.67 | 1 200 0.65 | 1 399 0.52 | 1 230 0.55 |
| glucose/ glycine | 5 532 1.12 | 5 364 1.05 | 5 564 0.74 | 2 195 0.86 | 5 396 0.73 | 4 622 0.65 | 1 227 0.63 | 1 454 0.78 | 1 285 0.77 |
| sucrose/ mannitol | 5 185 2.19 | 5 127 1.91 | 5 200 1.47 | 1 127 2.42 | 5 142 1.26 | 5 230 1.31 | 2 85 1.66 | 3 172 1.73 | 2 115 1.53 |
| maltose/ mannitol | 5 185 1.77 | 5 127 1.96 | 5 200 1.91 | 2 127 1.33 | 5 142 2.10 | 5 230 1.58 | 1 85 2.02 | 2 172 1.73 | 2 115 1.63 |
| lactose/ mannitol | 5 185 2.20 | 5 127 2.45 | 5 200 2.00 | 1 127 2.66 | 5 142 2.22 | 5 230 1.55 | 2 85 2.18 | 3 172 1.67 | 2 115 1.37 |

These data indicated twelve combinations (shaded boxes) which were chosen for further study based on cake quality, osmolality (300 mOsm/kg is isotonic), and HMW aggregate levels.

The twelve chosen formulations from Table II were optimized to be isotonic, and then were freeze-dried. All formulations contained 0.1 mg/ml rhIL-12, 0.02% polysorbate TWEEN-80, 10 mM sodium succinate, pH 5.6. Residual moisture, percent HMW aggregate (post-lyophilization) and cake quality (1=poor, 3=excellent) were measured. Osmolality was calculated. The results are reported in Table III.

Residual moisture analysis of the cakes indicated that the combinations provided sufficient dryness (<1%). Cake quality was generally good, but HMW aggregate levels were elevated. Optimization of the lyophilization cycle used in the generation of these samples could result in increased cake quality. Based on these data five candidates (shaded) were selected for further examination.

EXAMPLE 3

Examination of Effects of Polysorbate

Experiments determined that polysorbate TWEEN-80 helped to prevent precipitation of rhIL-12 during freeze/thaw cycles and shaking, as well as preventing adsorption of rhIL-12 to glass surfaces. Adsorption of a lyophilized dosage form after reconstitution is a distinct possibility due to the fact that rhIL-12 will likely be formulated at a very low protein concentration (10–100 μg/ml). To alleviate this potential problem, polysorbate TWEEN-80 was added to formulation candidates at a concentration of 0.02%. At this concentration, polysorbate TWEEN-80 provided the desired results.

Figure 8:
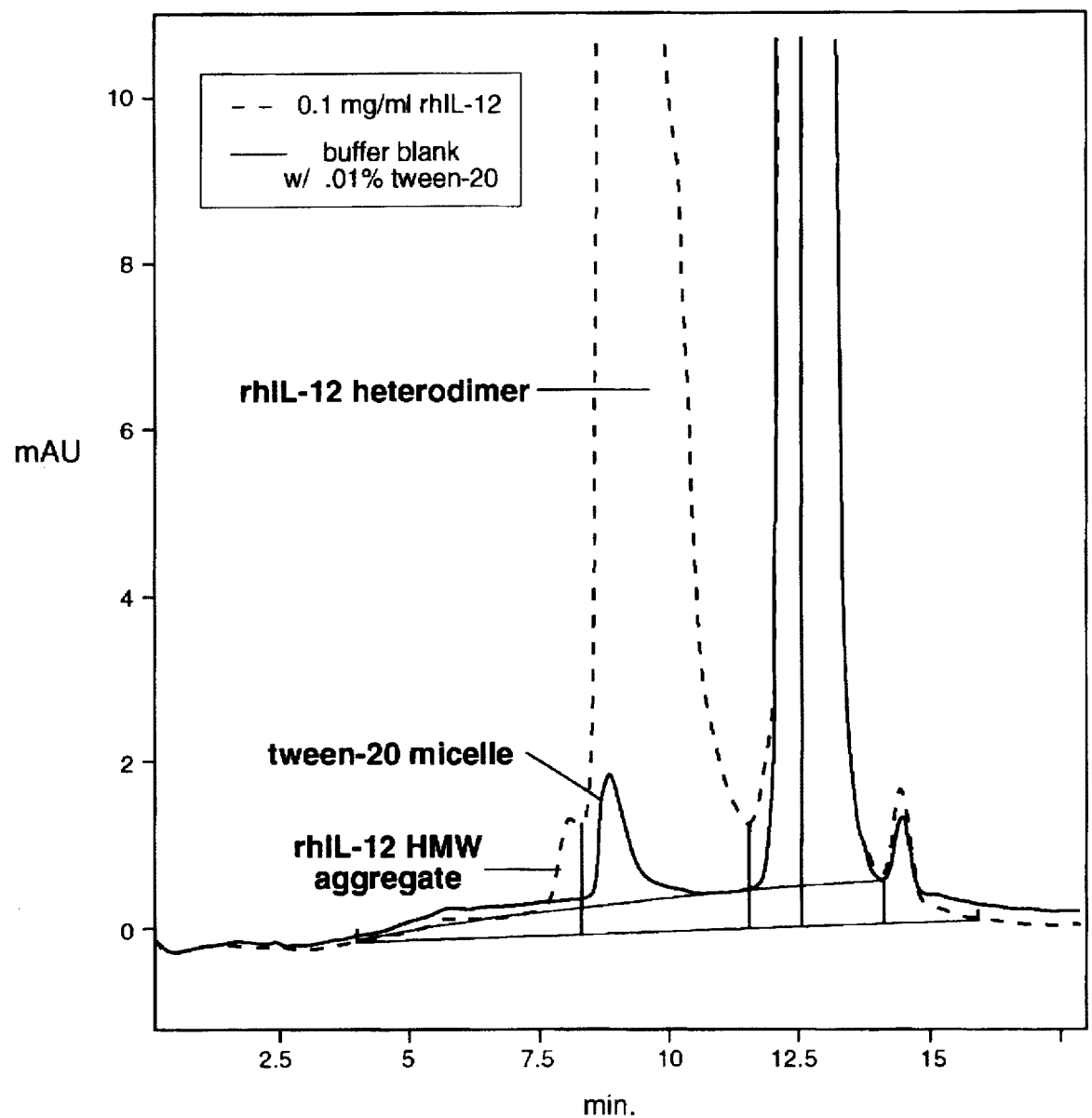
FIG. 8 shows an overlay of SEC traces from formulations containing tween-20, with and without 0.1 mg/ml rhIL-12.

However, at this particular concentration polysorbate TWEEN-80 also forms micelles that co-elute with HMW aggregate when resolved by SEC. FIG. 7 shows SEC traces from a 2×2 multi-variable matrix experiment and demonstrates that a polysorbate TWEEN-80 micelle co-elutes with the HMW aggregate. This artificially inflates the HMW species values at low protein concentrations, making the assay less accurate. Switching to polysorbate TWEEN-20 corrected this problem. FIG. 8 shows an overlay of SEC traces from formulations containing polysorbate TWEEN-20, with and without 0.1 mg/ml rhIL-12. This figure demonstrates that the polysorbate TWEEN-20 micelle does not co-elute with the HMW aggregate. However, it was necessary to establish that polysorbate TWEEN-20 performed as well as polysorbate TWEEN-80 with respect to handling and adsorption.

FIG. 9 shows the results of an adsorption study comparing polysorbate TWEEN-20 with polysorbate TWEEN-80.

TABLE III

| Formulation | Residual Moisture | % HMW (post-lyo) | Cake Quality | Osmolal. mOsm/kg |
|---|---|---|---|---|
| 0.5% sucrose 1.63% glycine | 0.12 | 7.15 | 2 | 293 |
| 1% sucrose 1.63% glycine | 0.90 | 6.00 | 1 | 307 |
| 0.5% maltose 1.63 glycine | 0.14 | 7.91 | 2 | 293 |
| 1% maltose 1.63% glycine | 1.90 | 7.35 | 1 | 307 |
| 0.5% glucose 1.63% glycine | −0.19 | 6.06 | 2 | 302 |
| 1% glucose 1.63% glycine | 1.34 | 6.57 | 1 | 300 |
| 1% sucrose 4.67% mannitol | 0.41 | 12.53 | 3 | 300 |
| 2% sucrose 4.15% mannitol | 0.56 | 9.88 | 3 | 300 |
| 1% maltose 4.67% mannitol | 0.42 | 11.71 | 3 | 300 |
| 2% maltose 4.15% mannitol | 0.50 | 8.90 | 3 | 300 |
| 1% lactose 4.67% mannitol | 0.44 | 7.52 | 3 | 300 |
| 2% lactose 4.15% mannitol | 0.64 | 11.40 | 3 | 300 | rhIL-12 at 2 and 5 µg/ml containing either polysorbate TWEEN-20 or polysorbate TWEEN-80 at 0.001% or 0.01% in 10 mM sodium succinate pH 5.6 was allowed to stand at room temperature in a 5 ml glass vial for 0, 3 and 7 days. Samples were analyzed by fluorescence spectroscopy (ex= 295 em=337) and compared to a standard curve (2 to 10 µg/ml also by fluorescence). Recoveries are based on day 0 data. These data demonstrate that tween-20 is as good as, if not better than, polysorbate TWEEN-80.

Figure 10:
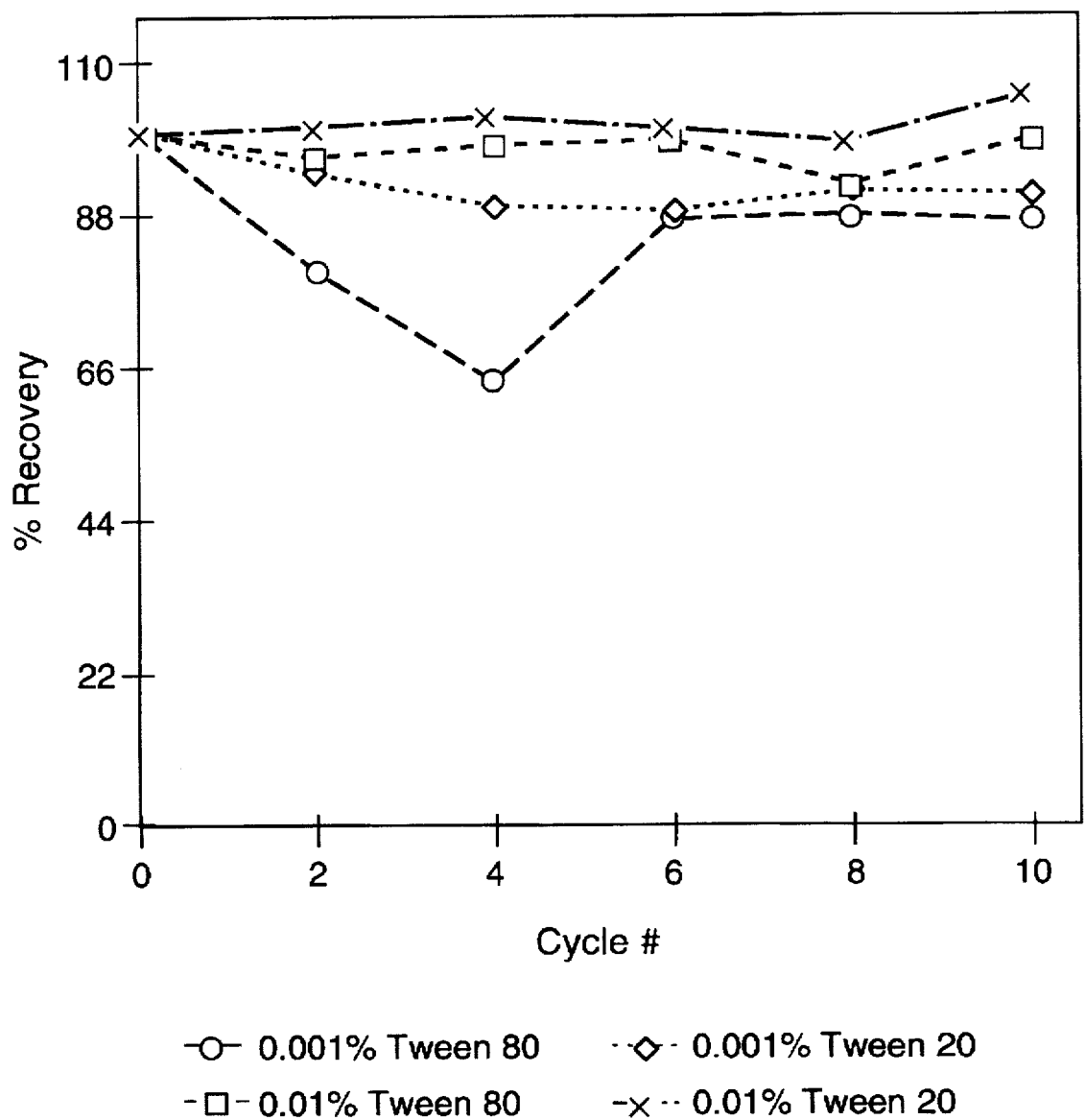
FIG. 10 shows the results of a freeze/thaw study comparing tween-20 with tween-80.

FIG. 10 shows the results of a freeze/thaw study comparing polysorbate TWEEN-20 with polysorbate TWEEN-80. rhIL-12 at 20 µgml containing either polysorbate TWEEN-20 or polysorbate TWEEN-80 at 0.001% or 0.01% in 10 mM sodium succinate pH 5.6 were taken through 10 freeze/thaw cycles.

Aliquots were taken at cycles 0, 2, 4, 6, 8 and 10 and were analyzed by fluorescence as described above for FIG. 9. Recoveries are based on the 0 cycle data. These data demonstrate that polysorbate TWEEN-20 performs as well as polysorbate TWEEN-80 in providing some cryoprotectant effects. Addition of either polysorbate TWEEN-20 or polysorbate TWEEN-80 was better than addition of no polysorbate.

Figure 11:
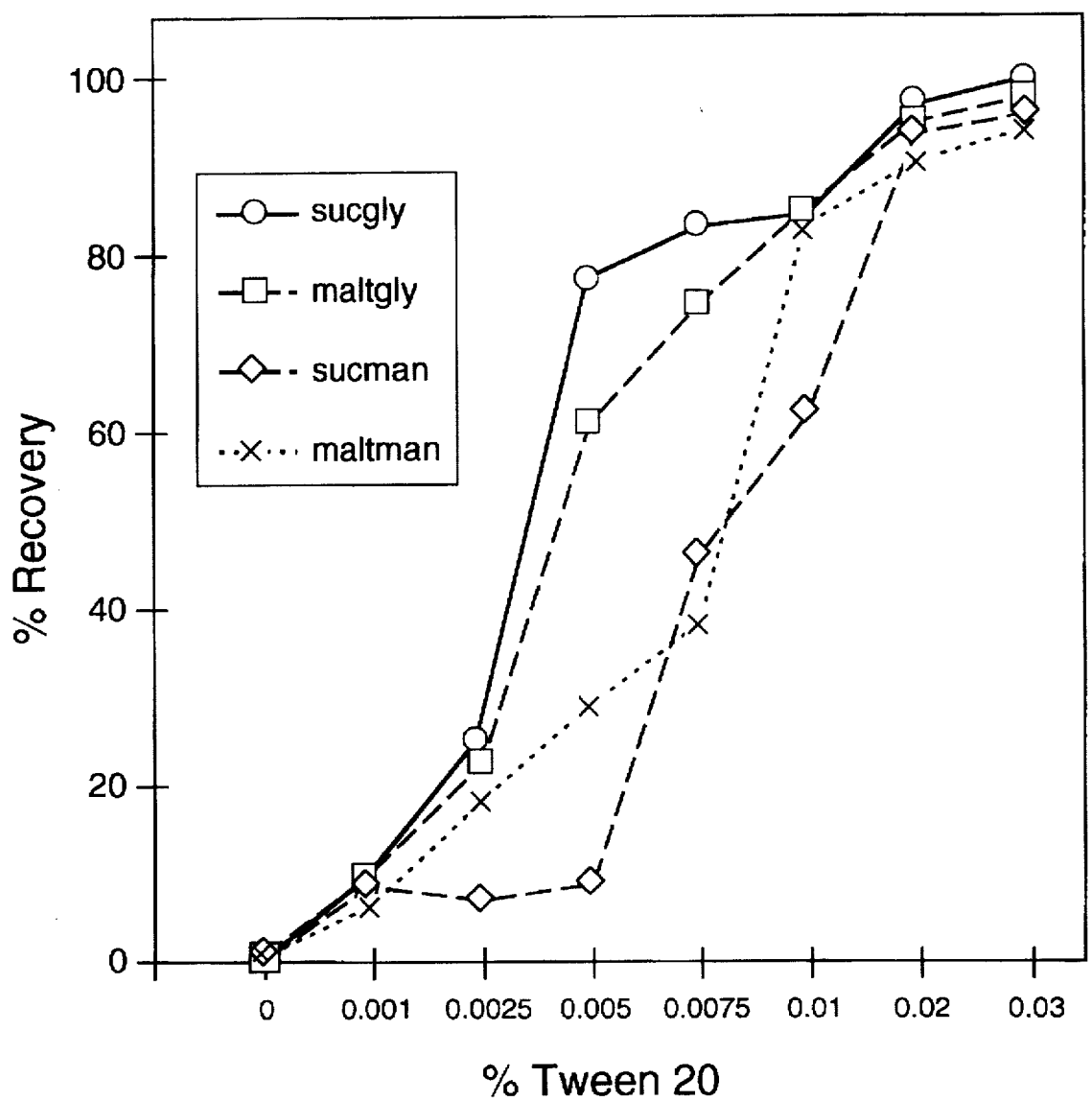
FIG. 11 shows the results of a shaking study of various rhIL-12 formulations.

FIG. 11 shows the results of a shaking study. rhIL-12 at 0.1 mg/ml in a variety of candidate formulations at seven different concentrations of polysorbate TWEEN-20 were shaken vigorously for 72 hours. The samples were filtered and assayed by reverse phase chromatography. Recovery is total protein based on samples that were not shaken.

EXAMPLE 4

Stability Studies

The stability of several formulations was studied over time. A sucrose/glycine formulation ("SG" or "SucGly") was used which contained 0.5% sucrose, 1.63% glycine, 0.01% polysorbate TWEEN-20, 10 mM sodium succinate, pH 5.6. A sucrose/mannitol formulation ("SM" or "SucMan") was used which contained 2.0% sucrose, 4.15% mannitol, 0.02% polysorbate TWEEN-20, 10 mM sodium succinate, pH 5.6. Both of these formulations were used to make test formulations containing three different protein concentrations (0.1 mg/ml, 0.05 mg/ml and 0.01 mg/ml rhIL-12). The various test formulations were stored at 4° C., 30° C. and 40° C. Samples were assayed for rhIL-12 concentration and HMW aggregate content at various time intervals.

FIGS. 12–14 show the progression of rhIL-12 concentration over time for the 0.1 mg/ml, 0.05 mg/ml and 0.01 mg/ml rhIL-12 test formulations, respectively. FIGS. 15–17 show the progression of HMW aggregate content over time for the 0.1 mg/ml, 0.05 mg/ml and 0.01 mg/ml rhIL-12 test formulations, respectively.

While the present invention has been described in terms of specific methods, formulations, and compositions, it is understood that variations and modifications will occur to those skilled in the art upon consideration of the present invention. Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed is:

1. A composition comprising about 1 to about 1000 µg/ml IL-12, about 2% sucrose, about 4.15% mannitol, about 10 mM sodium succinate, and about 0.02% polysorbate TWEEN-20, and having a pH of about 5.6.

2. The composition of claim 1 wherein said protein is present at a concentration of about 5 to about 500 µg/ml.

3. The composition of claim 1 wherein said composition is lyophilized.

4. The composition of claim 1 wherein said composition is lyophilized.

* * * * *